United States Patent
Hlavinka et al.

[11] Patent Number: 6,071,422
[45] Date of Patent: Jun. 6, 2000

[54] PARTICLE SEPARATION METHOD AND APPARATUS

[75] Inventors: Dennis Hlavinka, Golden; Frank Corbin, Littleton, both of Colo.

[73] Assignee: Cobe Laboratories, Inc., Lakewood, Colo.

[21] Appl. No.: 09/084,132

[22] Filed: May 26, 1998

Related U.S. Application Data

[60] Division of application No. 08/634,167, Apr. 18, 1996, Pat. No. 5,939,139, which is a continuation-in-part of application No. 08/423,578, Apr. 18, 1995, Pat. No. 5,674,173, and a continuation-in-part of application No. 08/423,583, Apr. 18, 1995, abandoned.

[51] Int. Cl.$^7$ .............................. B01D 21/26; B04B 1/00; B04B 9/10; B04B 11/02; C12N 1/00
[52] U.S. Cl. ..................... 210/782; 210/786; 210/787; 210/789; 210/806; 435/2; 435/372; 435/372.3; 494/5; 494/7; 494/36; 494/37; 494/45
[58] Field of Search ......................... 210/782, 786, 210/787, 789, 806; 435/2, 372, 372.3; 494/7, 36, 5, 37, 45

[56] References Cited

U.S. PATENT DOCUMENTS

| | | |
|---|---|---|
| 2,616,619 | 11/1952 | MacLeod . |
| 3,825,175 | 7/1974 | Sartory . |
| 4,091,989 | 5/1978 | Schlutz . |
| 4,187,979 | 2/1980 | Cullis et al. . |
| 4,268,393 | 5/1981 | Persidsky et al. . |
| 4,269,718 | 5/1981 | Persidsky . |
| 4,316,576 | 2/1982 | Cullis et al. . |
| 4,322,298 | 3/1982 | Perisdsky . |
| 4,350,283 | 9/1982 | Leonian . |
| 4,416,654 | 11/1983 | Schoendorfer et al. . |
| 4,425,112 | 1/1984 | Ito . |
| 4,464,167 | 8/1984 | Schoendorfer et al. . |
| 4,675,117 | 6/1987 | Neumann et al. . |
| 4,680,025 | 7/1987 | Kruger et al. . |
| 4,701,267 | 10/1987 | Watanabe et al. . |
| 4,708,710 | 11/1987 | Dunn, Jr. . |
| 4,708,712 | 11/1987 | Mulzet . |

(List continued on next page.)

FOREIGN PATENT DOCUMENTS

| | | |
|---|---|---|
| 057 907 | 8/1982 | European Pat. Off. . |
| 0 406 486 A1 | 1/1991 | European Pat. Off. . |
| 0 408 462 A2 | 1/1991 | European Pat. Off. . |
| 0 419 346 A2 | 3/1991 | European Pat. Off. . |
| 2658926 | 6/1978 | Germany . |
| 37 00 122 | 7/1988 | Germany . |
| WO 94/02157 | 2/1994 | WIPO . |
| WO 94/25086 | 11/1994 | WIPO . |
| WO 94/27698 | 12/1994 | WIPO . |
| WO 96/33023 | 10/1996 | WIPO . |
| WO 96/40402 | 12/1996 | WIPO . |
| WO 97/30748 | 8/1997 | WIPO . |
| WO 97/43045 | 11/1997 | WIPO . |

OTHER PUBLICATIONS

Maxim D. Persidsky et al., Separation of Platelet–rich Plasma by Modified Centrifugal Elutriation; Journal of Clinical Apheresis 1:18–24 (1982).

John F. Jemionek et al., Special Techniques for the Separation of Hemopoietic Cells, Current Methodology in Experimental Hematology, 1984, pp. 12–16.

J. Freedman et al., White Cell Depletion of Red Cell and Pooled Random–Donor Platelet Concentrates by Filtration and Residual Lymphocyte Subset Analysis, Transfusion, 1991, vol. 31, No. 5, pp. 433–440.

(List continued on next page.)

*Primary Examiner*—John Kim
*Attorney, Agent, or Firm*—Finnegan, Henderson, Farabow, Garrett & Dunner, L.L.P.

[57] ABSTRACT

An apparatus and method are disclosed for filtering or separating particles. The apparatus has a centrifuge rotor rotatable about an axis of rotation. A fluid chamber rotates with the rotor. A substance is supplied to the inlet of the chamber. A saturated fluidized bed of first particles forms within the fluid chamber and obstructs flow of second particles through the chamber. Additive substances alter sedimentation velocity of the first particles to modify the filtration characteristics of the saturated fluidized bed.

29 Claims, 13 Drawing Sheets

U.S. PATENT DOCUMENTS

| | | |
|---|---|---|
| 4,798,579 | 1/1989 | Penhasi . |
| 4,808,151 | 2/1989 | Dunn, Jr. et al. . |
| 4,851,126 | 7/1989 | Schoendorfer . |
| 4,885,137 | 12/1989 | Lork . |
| 4,936,820 | 6/1990 | Dennehey et al. . |
| 4,936,998 | 6/1990 | Nishimura et al. . |
| 4,939,081 | 7/1990 | Figdor et al. . |
| 4,939,087 | 7/1990 | Van Wie et al. . |
| 5,078,671 | 1/1992 | Dennehey et al. . |
| 5,089,146 | 2/1992 | Carmen et al. . |
| 5,100,564 | 3/1992 | Pall et al. . |
| 5,213,970 | 5/1993 | Lopez-Berestein et al. . |
| 5,224,921 | 7/1993 | Dennehey et al. . |
| 5,229,012 | 7/1993 | Pall et al. . |
| 5,282,982 | 2/1994 | Wells . |
| 5,298,171 | 3/1994 | Biesel . |
| 5,316,666 | 5/1994 | Brown et al. . |
| 5,316,667 | 5/1994 | Brown et al. . |
| 5,360,542 | 11/1994 | Williamson, IV et al. . |
| 5,362,291 | 11/1994 | Williamson, IV . |
| 5,370,802 | 12/1994 | Brown . |
| 5,397,479 | 3/1995 | Kass et al. . |
| 5,409,813 | 4/1995 | Schwartz . |
| 5,501,795 | 3/1996 | Pall et al. . |
| 5,529,691 | 6/1996 | Brown . |
| 5,547,591 | 8/1996 | Hagihara et al. . |
| 5,549,834 | 8/1996 | Brown . |
| 5,580,465 | 12/1996 | Pall et al. . |
| 5,587,070 | 12/1996 | Pall et al. . |
| 5,607,830 | 3/1997 | Biesel et al. . |
| 5,614,106 | 3/1997 | Payrat et al. . |
| 5,622,819 | 4/1997 | Herman . |
| 5,641,414 | 6/1997 | Brown . |
| 5,641,622 | 6/1997 | Lake et al. . |
| 5,643,786 | 7/1997 | Cohen et al. . |
| 5,674,173 | 10/1997 | Hlavinka et al. . |
| 5,722,926 | 3/1998 | Hlavinka et al. . |
| 5,906,570 | 5/1999 | Langley et al. ............ 494/45 |
| 5,913,768 | 8/1999 | Langley et al. ............ 494/7 |
| 5,939,319 | 8/1999 | Hlavinka et al. ............ 435/325 |
| 5,951,877 | 9/1999 | Langley et al. ............ 210/782 |

OTHER PUBLICATIONS

Nancy M. Heddle et al., The Role of the Plasma from Platelet Concentrates in Transfusion Reactions, The New England Journal of Medicine, vol. 331, No. 10, Sep. 8, 1994, pp. 625–628, 670 and 671.

A. Bruil et al., Asymmetric Membrane Filters for the Removal of Leukocytes From Blood, Journal of Biomed. Materials Research, vol. 25, 1459–1480, 1991.

Sunny Dzik, Leukodepletion Blood Filters: Filter Design and Mechanisms of Leukocyte Removal, Transfusion Medicine Reviews, vol. VII, No. 2, Apr. 1993, pp. 65–77.

Bernard J. Van Wie et al., The Effect of Hematocrit and Recycle on Cell Separations, Plasma Ther. Transfus. Technol. 1986; 7:373–388.

P.D. Drumheller et al., The Effects of RPM and Recycle on Separation Efficiency in a Clinical Blood Cell Centrifuge, Journal of Biomechanical Engineering, Nov. 1987, vol. 109, pp. 324–329.

R.J. Oxford et al., Monitoring and Automated Optimization of a Cell Centrifuge, IEEE/Eighth Annual Conference of the Engineering in Medicine and Biology Society, pp. 925–927 (Undated).

R.J. Oxford et al., Interface Dynamics in a Centrifugal Cell Separator, Transfusion, Nov.–Dec., 1988, vol. 28, Nov. 6, pp. 588–592.

A. Tulp et al., A Separation Chamber to Sort Cells and Cell Organelles by Weak Physical Forces, V.A. Sector–Shaped Chamber and Its Application to the Separation of Peripheral Blood Cells, Journal of Immunological Methods 69 (1984), pp. 281–295.

Robert J. Grabske, Separating Cell Populations by Elutriation, pp. 1–8 (Undated).

Carl G. Figdor et al., Theory and Practice of Centrifugal Elutriation (CE) Factors Influencing the Separation of Human Blood Cells, Cell Biophysics 5, 105–118 (1983).

P.E. Lindahl, On Counter Streaming Centrifugation in the Separation of Cells and Cell Fragments (1956), pp. 411–415.

C. Almici et al., Counterflow Centrifugal Elutriation: Present and Future, Bone Marrow Transplantation 1993, 12:105–108.

Richard J. Sanderson, Separation of Different Kinds of Nucleated Cells from Blood by Centrifugal Elutriation, Cell Separation Methods and Selected Applications, vol. 1, pp. 153–168 (1982).

P.C. Keng et al., Characterization of the Separation Properties of the Beckman Elutriator System, Cell Biophysics 3 (1981), pp. 41–56.

Biofil, Systems for Filtration of Haemocomponents (Undated).

Claes, F. Hogman, Leucocyte Depletion of Blood Components, 1994, pp. 1, 156–173.

A.S. Buchanan et al., Principle of a Counter–streaming Centrifuge for the Separation of Particles of Different Sizes, Nature, Apr. 24, 1948, pp. 648–649.

"Cost–Effectiveness of Leukocyte Depletion of Blood Components", Presented at the 1993 AABB Meeting Miami Beach, FL.

I. Sniecinski, Prevention of Immunologic and Infectious Complications of Transfusion by Leukocyte Depletion, Prevention of Complications of Transfusion Chapter 18; pp. 202–211 (Undated).

Benefits of Leukocyte Filtration for Red Cell and Platelet Blood Products, Transfusion Associated CMV (1994), pp. 1–18.

G. Stack et al., Cytokine Generation in Stored Platelet Concentrates, Transfusion, 1994; 34:20–25.

N. M. Heddle et al., A Prospective study to identify the risk factors associated with acute reactions to platelet and red cell transfusions; Transfusion, 1993; 33:794–797.

H. Brandwein et al., Asahi Sepacell PL10A Leukocyte Removal Filter:Efficiency with Random Donor Platelet Pools, PALL Technical Report (Undated).

J. Whitbread et al., Performance Evaluation of the Sepacell PL10A filter and Pall PXL 8 filter: Measurement of Leukocyte Residuals and Consistency, PALL Technical Report (Undated).

R. Brown et al., Evaluation of a new separation method utilizing plasma recirculation and autoelutriation, Transfusion, 1994; vol. 34, Supp.

Richard J. Sanderson et al., Design Principles for a Counterflow Centrifugation Cell Separation Chamber; Analytical Biochemistry 71, 615–622(1976).

Designed to Provide the Reliability and Performance to Harvest a High Yield Component Product, The Haemonetics V50 Apheresis System (Undated).

Haemonetics Mobile Collection System Owner's Operating and Maintenance Manual, 1991 pp. 3–2 through 3–7 and pp. 1–6.

E.A. Burgstaler et al., White Blood Cell Contamination of Apheresis Platelets Collected on the COBE Spectra, COBE Blood Component Technology (1992).

T.H. Price et al., Platelet Collection Using the COBE Spectra, COBE Blood Component Technology (1989).

Nancy Besso et al., Asahi Sepacell PL–10A Leukocyte Removal Filter: Effect of Post–Filtration Flush With Saline, PALL Technical Report (1991).

Harvey J. Brandwein et al., Asahi Sepacell PL–10A Leukocyte Removal Filter Description and Review of Claims, PALL Technical Report (1991).

"Lower is Better!", (flyer) PALL Biomedical Products Company (1994).

Judy H. Angelbeck, Adverse Reactions to Platelet Transfusion, Risks and Probable Causes (1994), pp. 1–14.

Centrifugual Elutriation, Beckman pp. 1–7, vi. (Undated).

AS 104 Cell Separator, Fresenius (Undated).

CS–3000 Blood Cell Separator, Powerful Technology, Fenwal Laboratories (Undated).

Baxter CS–3000 Plus Blood Cell Separator Operator's Manual (7–19–3–136) (Undated).

The Mobile Collection System gives you easier access to more donors than ever before, Haemonetics (Sep. 1992).

LRF6/LRF10, High Efficiency Leukocyte Removal Filter Systems For Platelets, PALL Biomedical Products Corporation (Undated).

J. Whitbread et al., Reduction of C3A Fragment Levels Following Leukodepletion Using a PALL PXL8 Filter (Undated).

T. A. Takahashi et al., Bradykinin Formation in a Platelet Concentrate Filtered with a Leukocyte–removal Filter Made of Nonwoven Polyester Fibers with a Negatively Charged Surface (Undated).

Baxter CS–3000 Plus Blood Cell Separator pp. 1–18 (Undated).

J. F. Jemionek, Variations in CCE Protocol for Cell Isolation, Elutriation, pp. 17–41 (Undated).

Brief Operating Instructions, Fresenius MT AS 104 blood cell separator, 4/6.90(OP) (Undated).

English language abstract of SU 1725117 A(Undated).

English language abstract of SU 1255136 (Undated).

English language abstract of SU 1236366 (Undated).

English language abstract of SU 1091071 (Undated).

English language abstract of DE 3734170 (Undated).

Multi Chamber Counterflow Centrifugation System, Dijkstra Vereenigde B.V., 13 pgs (Undated).

Baxter CS–3000 Plus Blood Cell Separator, Technology With a Mind You Can Own, 1990.

Aart Plas, Theo de Witte, Hans Wessels, and Clements Haanen, "A New Multi–chamber Counterflow Centrifugation Rotor with High–separation Capacity and Versatile Potentials," Experimental Hematology 16:355–359 (1988) International Society for Experimental Hematology.

Micheal G. Kauffman, Stephen J. Noga, Thomas J. Kelly, and Albert D. Donnenberg, "Isolation of Cell Cycle Fractions by Counterflow Centrifugal Elutriation," Analytical Biochemistry 191, 41–46 (1990).

A. Faradji, A. Bohbot, M. Schmitt–Goguel, J.C. Siffert, S. Dumont, M.L. Wiesel, Y. Piemont, A. Eischen, J.P. Bergerat J. Bartholeyns, P. Poindron, J.P. Witz, F. Oberling, "Large Scale Isolation of Human Blood Monocytes by Continuous Flow Centrifugation Leukapherisis and Counterflow Centrifugation Elutriation for Adoptive Cellular Immunotherapy in Cancer Patients," Journal of Immunological Methods 174 (1994) 297–309.

Ino K. Gao, Stephn J. Noga, John E. Wagner, Carol A. Cremo, Janice Davis and Albert D. Donnenberg, "Implementation of a Semiclosed Large Scale Centrifugal Elutriation System," Journal of Clinical Apheresis 3:154–160 (1987).

Owen M. Griffith, "Separation of T and B Cells from Human Peripheral Blood by Centrifugal Elutriation," Analytical Biochemistry 87, 97–107 (1978).

Carl G. Figdor, Willy S. Bont, Ivo Touw, Johan de Roos, Eddy E. Roosnek and Jan E. de Vries, "Isolation of Functionally Different Human Monocytes by Counterflow Centrifugation Elutriation," Blood, vol. 60, No. 1, 46–52 (Undated).

Bernard John Van Wie, Conceptualization and Evaluation of Techniques for Centrifugal Separation of Blood Cells: Optimum Process Conditions, Recycle and Stagewise Processing, Dissertation, 1982, pp. 27–58.

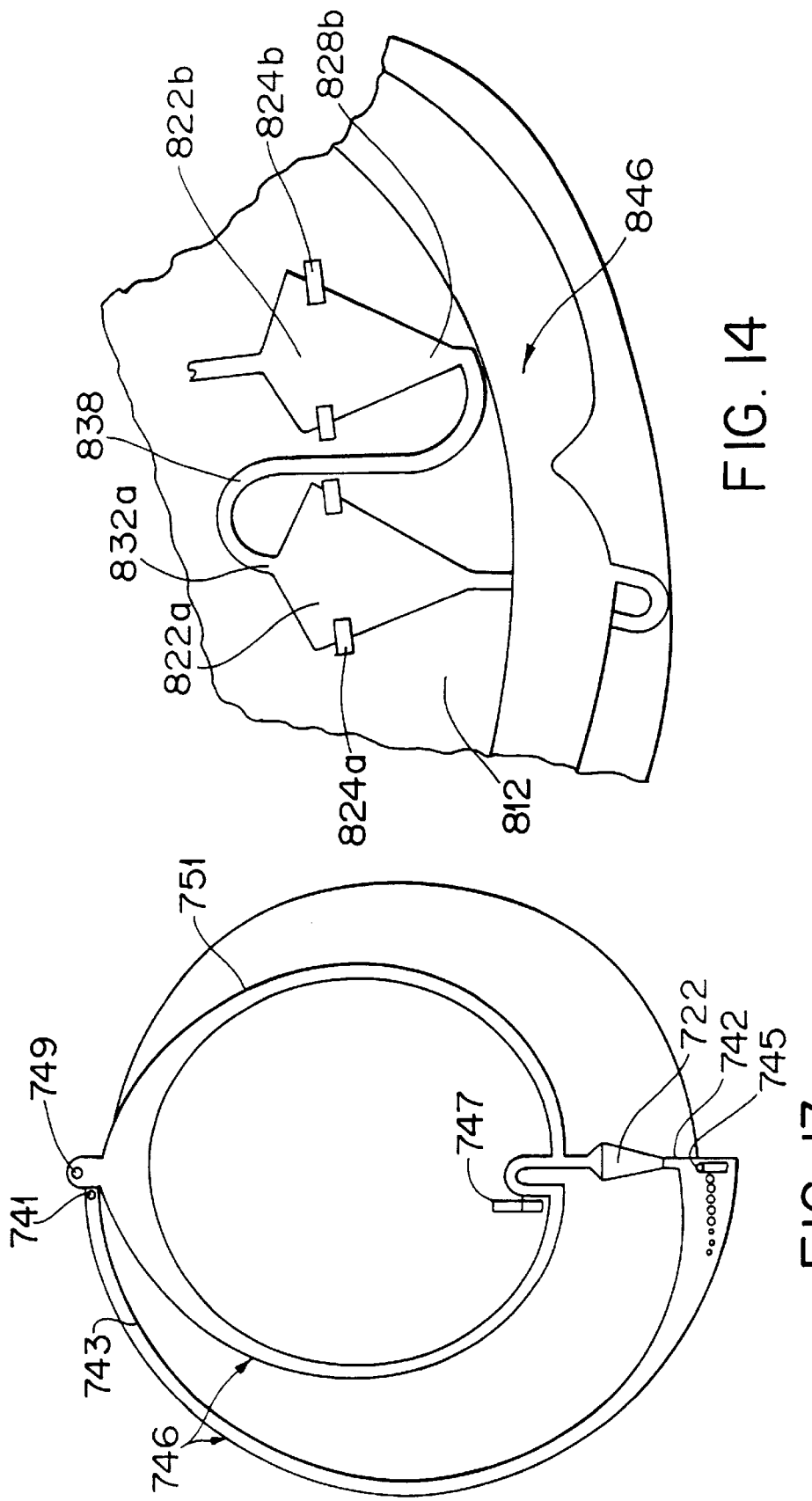

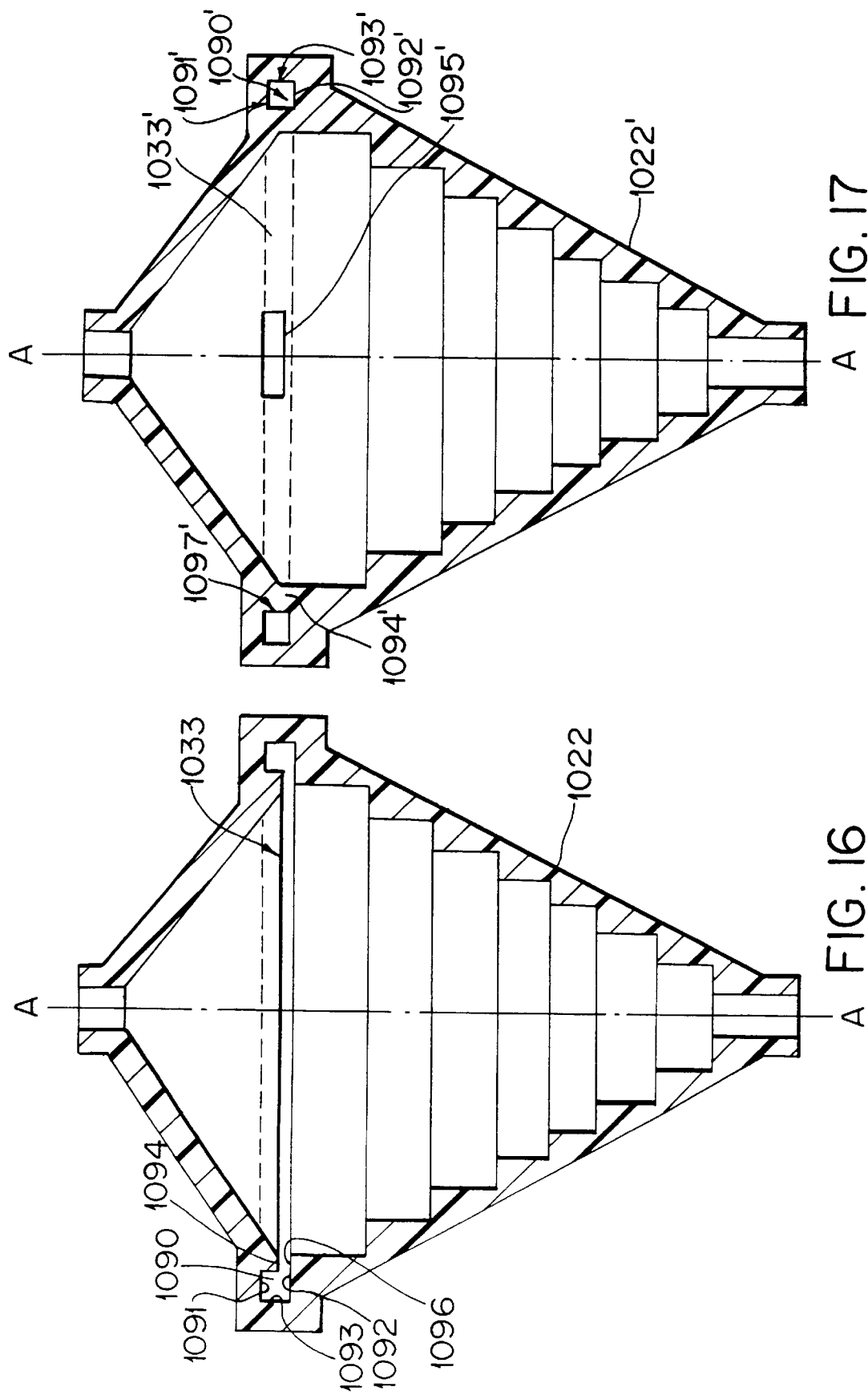

PARTICLE SEPARATION METHOD AND APPARATUS

This application is a divisional of U.S. patent application Ser. No. 08/634,167, filed on Apr. 18, 1996, U.S. Pat. No. 5,939,139 which is a continuation-in-part of U.S. patent application Ser. No. 08/423,578, filed on Apr. 18, 1995 now U.S. Pat. No. 5,674,173, and is also a continuation-in part of U.S. patent application Ser. No. 08/423,583, filed on Apr. 18, 1995 (now abandoned). The entire disclosures of U.S. patent application Ser. Nos. 08/423,578, 08/423,583 and 08/643,167 are incorporated herein by reference.

BACKGROUND OF THE INVENTION

1. Field of the Invention

The present invention relates to a method and apparatus for separating first particles from second particles. The invention has particular advantages in connection with separating stem cells, tumor cells, T cells, and red blood cells.

2. Description of the Related Art

In many different fields, liquids carrying particle substances must be filtered or processed to obtain either a purified liquid or purified particle end product. In its broadest sense, a filter is any device capable of removing or separating particles from a substance. Thus, the term "filter" as used herein is not limited to a porous media material but includes many different types of processes where particles are either separated from one another or from liquid.

In the medical field, it is often necessary to filter blood. Whole blood consists of various liquid constituents and particle constituents. Sometimes, the particle constituents are referred to as "formed elements". The liquid portion of blood is largely made up of plasma, and the particle constituents include red blood cells (erythrocytes), white blood cells (including leukocytes), and platelets (thrombocytes). While these constituents have similar densities, their average density relationship, in order of decreasing density, is as follows: red blood cells, white blood cells, platelets, and plasma. In addition, the particle constituents are related according to size, in order of decreasing size, as follows: white blood cells, red blood cells, and platelets. The size of red blood cells, however, may vary because red blood cells osmotically change size depending on the hypotonicity or hypertonicity of a liquid, such as plasma, in which the red blood cells are disbursed. When hypotonicity of plasma increases, the red blood cells osmotically become larger. Conversely, when hypertonicity of plasma increases, the red blood cells osmotically become smaller. Most current purification devices rely on density and size differences or surface chemistry characteristics to separate and/or filter the blood components.

Numerous therapeutic treatments require groups of particles to be removed from whole blood before either liquid or particle components can be infused into a patient. For example, cancer patients often require platelet transfusions after undergoing ablative, chemical, or radiation therapy. In this procedure, donated whole blood is processed to remove platelets and these platelets are then infused into the patient. However, if a patient receives an excessive number of foreign white blood cells as contamination in a platelet transfusion, the patient's body may reject the platelet transfusion, leading to a host of serious health risks.

Typically, donated platelets are separated or harvested from other blood components using a centrifuge. The centrifuge rotates a blood reservoir to separate components within the reservoir using centrifugal force. In use, blood enters the reservoir while it is rotating at a very rapid speed and centrifugal force stratifies the blood components, so that particular components may be separately removed. Centrifuges are effective at separating platelets from whole blood, however they typically are unable to separate all of the white blood cells from the platelets. Historically, blood separation and centrifugation devices are typically unable to consistently (99% of the time) produce platelet product that meets the "leukopoor" standard of less than $5 \times 10^6$ white blood cells for at least $3 \times 10^{11}$ platelets collected.

Because typical centrifuge platelet collection processes are unable to consistently and satisfactorily separate white blood cells from platelets, other processes have been added to improve results. In one procedure, after centrifuging, platelets are passed through a porous woven or non-woven media filter, which may have a modified surface, to remove white blood cells. However, use of the porous filter introduces its own set of problems. Conventional porous filters may be inefficient because they may permanently remove or trap approximately 5–20% of the platelets. These conventional filters may also reduce "platelet viability," meaning that once passed through a filter a percentage of the platelets cease to function properly and may be partially or fully activated. In addition, porous filters may cause the release of brandykinin, which may lead to hypotensive episodes in a patient. Porous filters are also expensive and often require additional time consuming manual labor to perform a filtration process.

Although porous filters are effective in removing a substantial number of white blood cells, they have drawbacks. For example, after centrifuging and before porous filtering, a period of time must pass to give activated platelets time to transform to a deactivated state. Otherwise, the activated platelets are likely to clog the filter. Therefore, the use of porous filters is not feasible in on-line processes.

Another separation process is one known as centrifugal elutriation. This process separates cells suspended in a liquid medium without the use of a membrane filter. In one common form of elutriation, a cell batch is introduced into a flow of liquid elutriation buffer. This liquid which carries the cell batch in suspension, is then introduced into a funnel-shaped chamber located in a spinning centrifuge. As additional liquid buffer solution flows through the chamber, the liquid sweeps smaller sized, slower-sedimenting cells toward an elutriation boundary within the chamber, while larger, faster-sedimenting cells migrate to an area of the chamber having the greatest centrifugal force.

When the centrifugal force and force generated by the fluid flow are balanced, the fluid flow is increased to force slower-sedimenting cells from an exit port in the chamber, while faster-sedimenting cells are retained in the chamber. If fluid flow through the chamber is increased, progressively larger, faster-sedimenting cells may be removed from the chamber.

Thus, centrifugal elutriation separates particles having different sedimentation velocities. Stoke's law describes sedimentation velocity (SV) of a spherical particle as follows:

$$SV = \frac{2}{9} \frac{r^2 (\rho_p - \rho_m) g}{\eta}$$

where, r is the radius of the particle, $\rho_p$ is the density of the particle, $\rho_m$ is the density of the liquid medium, $\eta$ is the viscosity of the medium, and g is the gravitational or centrifugal acceleration. Because the radius of a particle is raised to the second power in the Stoke's equation and the density of the particle is not, the size of a cell, rather than its density, greatly influences its sedimentation rate. This explains why larger particles generally remain in a chamber during centrifugal elutriation, while smaller particles are released, if the particles have similar densities.

As described in U.S. Pat. No. 3,825,175 to Sartory, centrifugal elutriation has a number of limitations. In most of these processes, particles must be introduced within a flow of fluid medium in separate discontinuous batches to allow for sufficient particle separation. Thus, some elutriation processes only permit separation in particle batches and require an additional fluid medium to transport particles. In addition, flow forces must be precisely balanced against centrifugal force to allow for proper particle segregation.

Further, a Coriolis jetting effect takes place when particles flow into an elutriation chamber from a high centrifugal field toward a lower centrifugal field. The fluid and particles turbulently collide with an inner wall of the chamber facing the rotational direction of the centrifuge. This phenomenon mixes particles within the chamber and reduces the effectiveness of the separation process. Further, Coriolis jetting shunts flow along the inner wall from the inlet directly to the outlet. Thus, particles pass around the elutriative field to contaminate the end product.

Particle mixing by particle density inversion is an additional problem encountered in some prior elutriation processes. Fluid flowing within the elutriation chamber has a decreasing velocity as it flows in the centripetal direction from an entrance port toward an increased cross sectional portion of the chamber. Because particles tend to concentrate within a flowing liquid in areas of lower flow velocity, rather than in areas of high flow velocity, the particles concentrate near the increased cross-sectional area of the chamber. Correspondingly, since flow velocity is greatest adjacent the entrance port, the particle concentration is reduced in this area. Density inversion of particles takes place when the centrifugal force urges the particles from the high particle concentration at the portion of increased cross-section toward the entrance port. This particle turnover reduces the effectiveness of particle separation by elutriation.

In addition to red and white blood cells, plasma, and platelets, human blood also includes other particle components, such as T cells, stem cells, and, in some cases, tumor cells. These cells have substantially similar densities, but different sedimentation velocities and sizes. Generally, stem cells are larger than T cells and smaller than tumor cells. Some tumor cells (approximately 30%), however, are smaller than stem cells.

Existing purification devices are capable of purifying peripheral blood to isolate what is known as a peripheral cell collection for transfusion or reinfusion purposes. The peripheral cell collection typically includes primarily plasma, red blood cells, stem cells, and T cells, and may also include tumor cells if the donor's blood included such cells. Although transfusion of a peripheral cell collection is a common medical treatment, transfusion of a large number of T cells or tumor cells into a patient may have adverse consequences. Removal of T cells and tumor cells from a peripheral cell collection or whole blood before transfusion, however, is extremely difficult.

After undergoing a therapeutic treatment, such as chemotherapy or radiation therapy to eliminate cancerous tumor cells, cancer patients often receive a peripheral cell or bone marrow transfusion to replace stem cells destroyed as a side effect of the treatment. To reduce risks associated with infusing blood components from a foreign donor, some of these transfusions are autologous, where blood components collected from the patient are later reinfused back to the patient.

Blood components initially collected from cancer patients may include cancerous tumor cells, which are then infused back into the cancer patient during reinfusion. This reinfusion of tumor cells may diminish the effectiveness of therapeutic treatments aimed at reducing cancerous tumors in a patient's body.

Another type of transfusion, known as allogenic transfusion, involves collecting blood components from a donor and then infusing the collected blood components into a recipient who is different from the donor. Sometimes, however, the recipient of an allogenic transfusion experiences a disease commonly known as graft versus host disease. In graft versus host disease, T cells, which may accompany the blood components, are infused into the recipient and "recognize" that the recipient's body is "foreign" from that of the donor's. These T cells "attack" healthy cells in the recipient's body, rather than performing a normal immunological protective function.

Prior attempts to separate stem cells from tumor cells or separate stem cells from T cells prior to reinfusion have had limited success. In one separation method, a selective antibody is introduced into a collected blood component sample. The selective antibody chemically attaches to stem cells in the collection to "mark" them. To separate the marked stem cells from the remaining blood components, the collected blood components are passed between stationary beads coated with a material which chemically bonds with the selective antibody. These chemical bonds retain the marked stem cells on the beads to filter them from the remaining blood components. To remove the marked stem cells from the beads, a chemical solution is flushed through the beads to break the chemical bonds between the material and selective antibody. This separation process, however, is extremely expensive, tedious, and time consuming.

Centrifugal elutriation has been used to separate tumor cells from stem cells or to separate T cells from stem cells. With existing elutriation devices, however, this is time consuming, difficult, and of limited effectiveness.

For these and other reasons, there is a need to improve particle separation.

SUMMARY OF THE INVENTION

The present invention is directed to an apparatus and method that substantially obviate one or more of the limitations and disadvantages of the related art. To achieve these and other advantages and in accordance with the purpose of the invention, as embodied and broadly described herein, first particles and second particles are separated from each other using a centrifuge and fluid chamber that rotates with the centrifuge. Centrifuge rotation is controlled, and the sedimentation velocity of the first particles is altered. A quantity of these first particles pass into the inlet of the rotating fluid chamber and form a saturated fluidized bed within the fluid chamber. A liquid carrying at least a quantity of the second particles is directed into the fluid chamber while the bed within the chamber is maintained. The bed substantially prevents the second particles from leaving the chamber while substantially permitting passage of the liquid and a portion of the first particles.

In an aspect of the invention, the first particles include red blood cells and the second particles include cells chosen from a group consisting of stem cells and tumor cells.

In another aspect, the invention includes a method of separating first particles from second particles having a sedimentation velocity different from that of the first particles. The method comprises the steps of altering sedimentation velocity of third particles, forming within a fluid chamber a saturated fluidized bed of third particles, and obstructing with the saturated fluidized third particle bed movement of the second particles through the fluid chamber while permitting liquid and the first particles to pass through the fluid chamber.

In a further aspect, the method of the invention comprises the steps of flowing liquid having the first, second, and third particles into a fluid chamber and forming a saturated fluidized bed of the third particles within the fluid chamber. The saturated fluidized third particle bed obstructs flow of the second particles through the fluid chamber. The method also includes the step of permitting the liquid, the first particles, and a portion of the third particles to pass through the fluid chamber.

In another aspect, the method includes an additional step of separating particles flowing from the outlet of the fluid chamber from the liquid flowing from the outlet of the fluid chamber.

In addition to the method highlighted above, the invention also includes an apparatus for separating first particles from second particles. The apparatus comprises a motor and a centrifuge rotor coupled to the motor for rotation about an axis of rotation. A holder is provided for holding a fluid chamber on the rotor with an outlet of the fluid chamber positioned closer to the axis of rotation than an inlet of the fluid chamber. First and second particles are supplied to the inlet of the fluid chamber, as are substances that alter sedimentation velocity of the second particles. In addition, the apparatus includes structure for controlling at least one of the motor and substances supplied to the fluid chamber in order to maintain a saturated fluidized bed of first particles within the fluid chamber and to cause second particles to be retained in the fluid chamber.

In another variation of the apparatus, structure is provided for separating particles and liquid flowing from the outlet of the fluid chamber.

According to a further aspect of the present invention, the bed forming particles may comprise particles osmotically responsive to the concentration of a solute dissolved in a liquid in which the second particles are dispersed. In accordance with this aspect of the invention, the size, and thus the settling velocity, of the bed forming particles are adjusted by adjusting the solute concentration thereby adjusting the separation characteristics of the particles in the fluid chamber.

It is to be understood that both the foregoing general description and the following detailed description are exemplary, and are intended to provide further explanation of the invention as claimed. The accompanying drawings are included to provide a further understanding of the invention and are incorporated in and constitute a part of this specification. The drawings illustrate embodiments of the invention and, together with the description, serve to explain the principles of the invention.

BRIEF DESCRIPTION OF THE DRAWINGS

FIG. 13 illustrates a separation chamber and fluid chamber in another embodiment of the invention;

FIG. 14 is a partial view of a centrifuge apparatus including a separation chamber and multiple fluid chambers in a further embodiment of the invention;

FIG. 16 is a cross-sectional view of a fifth alternative embodiment of the fluid chamber of FIG. 2;

FIG. 17 is a cross-sectional view of a sixth alternative embodiment of the fluid chamber of FIG. 16;

DESCRIPTION OF THE PREFERRED EMBODIMENTS

Figure 1:
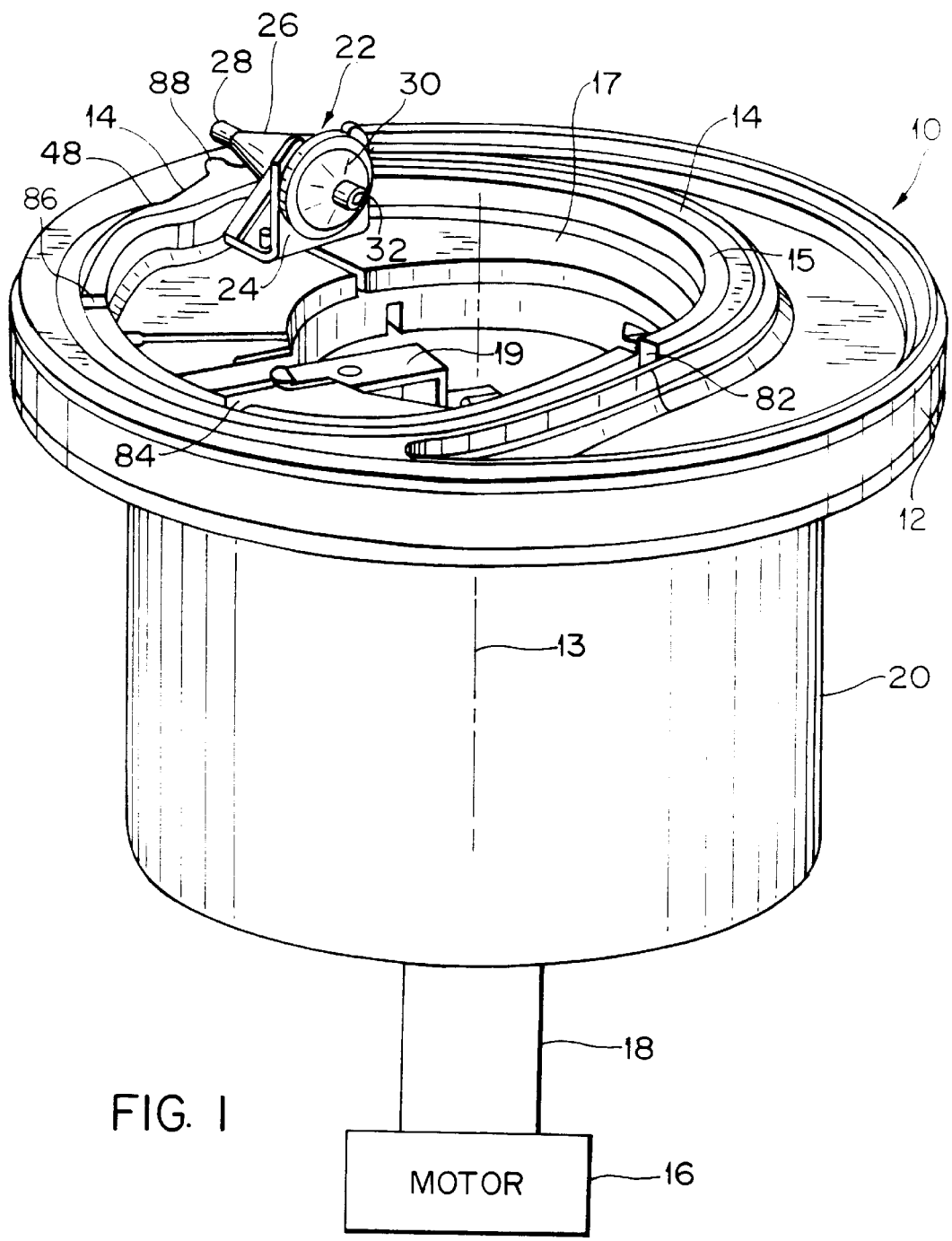
FIG. 1 is a perspective view of a centrifuge apparatus in accordance with a embodiment of the invention.

Reference will now be made in detail to the present preferred embodiments of the invention illustrated in the accompanying drawings.

An embodiment of the present invention is described by referring to its use with a COBE® SPECTRA™ two stage sealless blood component centrifuge manufactured by the assignee of the invention. The COBE® SPECTRA™ centrifuge incorporates a one-omega/two-omega sealless tubing connection as disclosed in U.S. Pat. No. 4,425,112 to Ito, the entire disclosure of which is incorporated herein by reference. The COBE® SPECTRA™ centrifuge also uses a two-stage blood component separation channel substantially as disclosed in U.S. Pat. No. 4,708,712 to Mulzet, the entire disclosure of which is also incorporated herein by reference. Although the embodiment of the invention is described in combination with the COBE® SPECTRA™ centrifuge, this description is not intended to limit the invention in any sense.

As will be apparent to one having skill in the art, the present invention may be advantageously used in a variety of centrifuge devices commonly used to separate blood into its components. In particular, the present invention may be used with any centrifugal apparatus that employs a component collect line such as a platelet collect line or a platelet rich plasma line, whether or not the apparatus employs a two stage or a one-omega/two-omega sealless tubing connection.

In accordance with the invention there is provided an apparatus for filtering first particles from a liquid, comprising a centrifuge rotor coupled to a motor for rotating the centrifuge rotor about an axis of rotation. As embodied herein and illustrated in FIG. 1, centrifuge 10 includes a rotor 12. The rotor 12 has an annular groove or passageway 14 having an open upper surface adapted to receive a conduit or channel 44 of a tubing set 70 shown in FIG. 4. The passageway 14 completely surrounds the rotor's axis of rotation 13 and is bounded on an inner surface by wall 15 positioned on a top surface 17 of rotor 12. A motor 16 is coupled to rotor 12 to rotate the rotor 12 about the axis of rotation 13. This coupling is accomplished directly or indirectly through a shaft 18 connected to an arm 19 that mounts to the rotor 12. Alternately, the shaft 18 may be coupled to the motor 16 through a gearing transmission (not shown). A shroud 20 is positioned on the rotor 12 to protect the motor 16 and shaft 18.

In accordance with the present invention, a holder is provided for holding a fluid chamber on the rotor with an outlet of the fluid chamber positioned closer to the axis of rotation than an inlet of the fluid chamber. As embodied herein and as illustrated in FIG. 1, the holder may include a mounting bracket 24 for maintaining a fluid chamber 22 on rotor 12 with an outlet 32 generally positioned closer to the rotation axis 13 than an inlet 28. The fluid chamber 22 fits within the mounting bracket 24 as illustrated in FIG. 1. The fluid chamber 22 may also be secured to the rotor 12 at alternate locations, such as beneath passageway 14. The fluid chamber 22 may be constructed of a transparent or translucent copolyester plastic, such as PETG, to allow viewing of the contents within the chamber interior with the aid of an optional strobe (not shown) during a centrifuge procedure.

Figure 2:
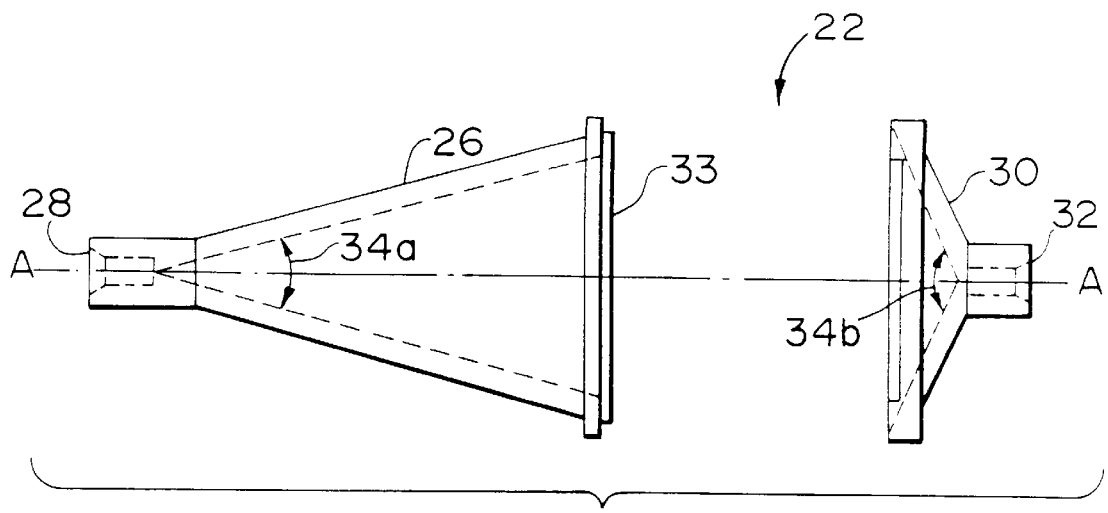
FIG. 2 is an exploded side view of a fluid chamber shown in FIG. 1.

As illustrated in FIG. 2, the fluid chamber 22 is formed by joining a first chamber section 26 having the inlet 28 to a second chamber section 30 having the outlet 32. The inlet 28 and outlet 32 are arranged along a longitudinal axis A—A.

In an embodiment of the invention the fluid chamber 22 has an interior volume of about 14.5 ml., although this parameter may be increased or decreased depending on the particular application. The interior of the first chamber section 26 has a frustoconical shape with a conical angle 34a of approximately 30 degrees. The interior of the second chamber section 30 also has a frustoconical shape having a conical angle 34b of approximately 120 degrees. These angles may be varied. For example, the conical angle 34b may range from approximately 90 to 120 degrees and the conical angle 34a may range from approximately 30 to 90 degrees.

The volume of the fluid chamber 22 should be at least large enough to accommodate enough platelets to provide a saturated fluidized particle bed (described below) for a particular range of flow rates, particle sizes, and centrifuge rotor 12 speeds.

Preferably, the fluid chamber interior has a maximum cross-sectional area 33 located at a position intermediate the inlet 28 and outlet 32 where sections 26, 30 join. The cross sectional area of the fluid chamber interior decreases or tapers from the maximum cross-sectional area 33 in both directions along axis A—A. Although the fluid chamber 22 is depicted with two sections 26, 30 having frustoconical interior shapes, the interior shapes may be paraboloidal, or of any other shape having a major cross-sectional area greater than the inlet or outlet area. The fluid chamber 22 may be constructed from a unitary piece of plastic rather than from separate sections.

Figure 3:
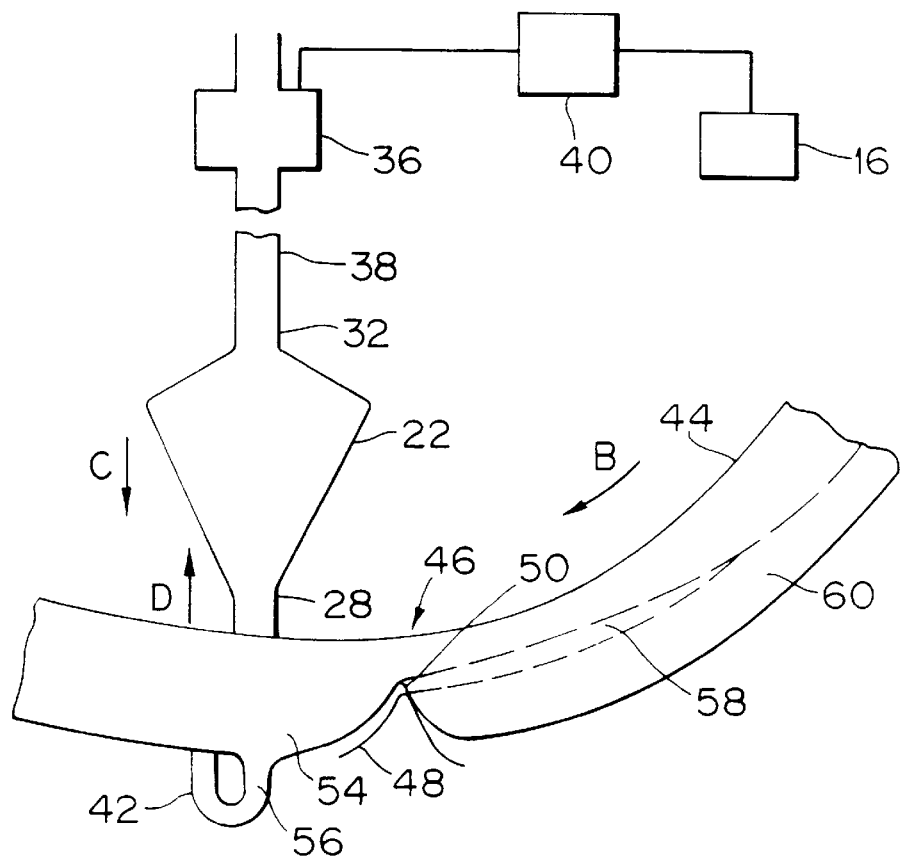
FIG. 3 is a partial schematic view of the apparatus of FIG. 1 illustrating a detailed view of components of the apparatus.

In accordance with the present invention, there is also provided means for supplying a substance to the inlet of the fluid chamber. As embodied herein and as schematically illustrated in FIG. 3, a pump 36 is fluidly connected to the fluid chamber 22 through outflow tubing 38. The pump 36 draws fluid and particles from the outlet 32 of the fluid chamber 22. The pump 36 is preferably a peristaltic pump or impeller pump configured to prevent significant damage to blood components, but any fluid pumping or drawing device may be provided. In an alternative embodiment (not shown), the pump 36 may be fluidly connected to the inlet of the fluid chamber 22 to directly move substances into and through the fluid chamber 22. The pump 22 may be mounted at any convenient location.

In accordance with the invention there is also provided means for controlling the motor and/or the supply means to maintain a saturated fluidized bed of second particles within the fluid chamber and to cause first particles to be retained in the chamber. As embodied herein and illustrated in FIG. 3, the controlling means may include a controller 40 connected to both the centrifuge motor 16 and the pump 36. As explained in detail below, during a centrifuge operation, controller 40 maintains a saturated fluidized particle bed within the fluid chamber 22 to separate particles. Controller 40 may include a computer having programmed instructions provided by a ROM or RAM as is commonly known in the art.

The controller 40 may vary the rotational speed of the centrifuge rotor 12 by regulating frequency, current, or voltage of the electricity applied to the motor 16. Alternatively, the rotor speed can be varied by shifting the arrangement of a transmission (not shown), such as by changing gearing to alter a rotational coupling between the motor 16 and rotor 12. The controller 40 may receive input from a rotational speed detector (not shown) to constantly monitor the rotor speed.

The controller 40 may also regulate the pump 36 to vary the flow rate of the substance supplied to the fluid chamber 22. For example, the controller 40 may vary the electricity provided to the pump 36. Alternatively the controller 40 may vary the flow rate to the chamber 22 by regulating a valving structure (not shown) positioned either within an inflow tubing 42 connected to the inlet 28 or within outflow tubing 38. The controller 40 may receive an input from a flow detector (not shown) positioned within the inflow tubing 42 to monitor the flow rate of substances entering the fluid chamber 22. Although a single controller 40 having multiple operations is schematically depicted in the embodiment shown in FIG. 3, the control means of the invention may include any number of individual controllers, each for performing a single function or a number of functions. The controller 40 may control flow rates in many other ways as is known in the art.

Figure 4:
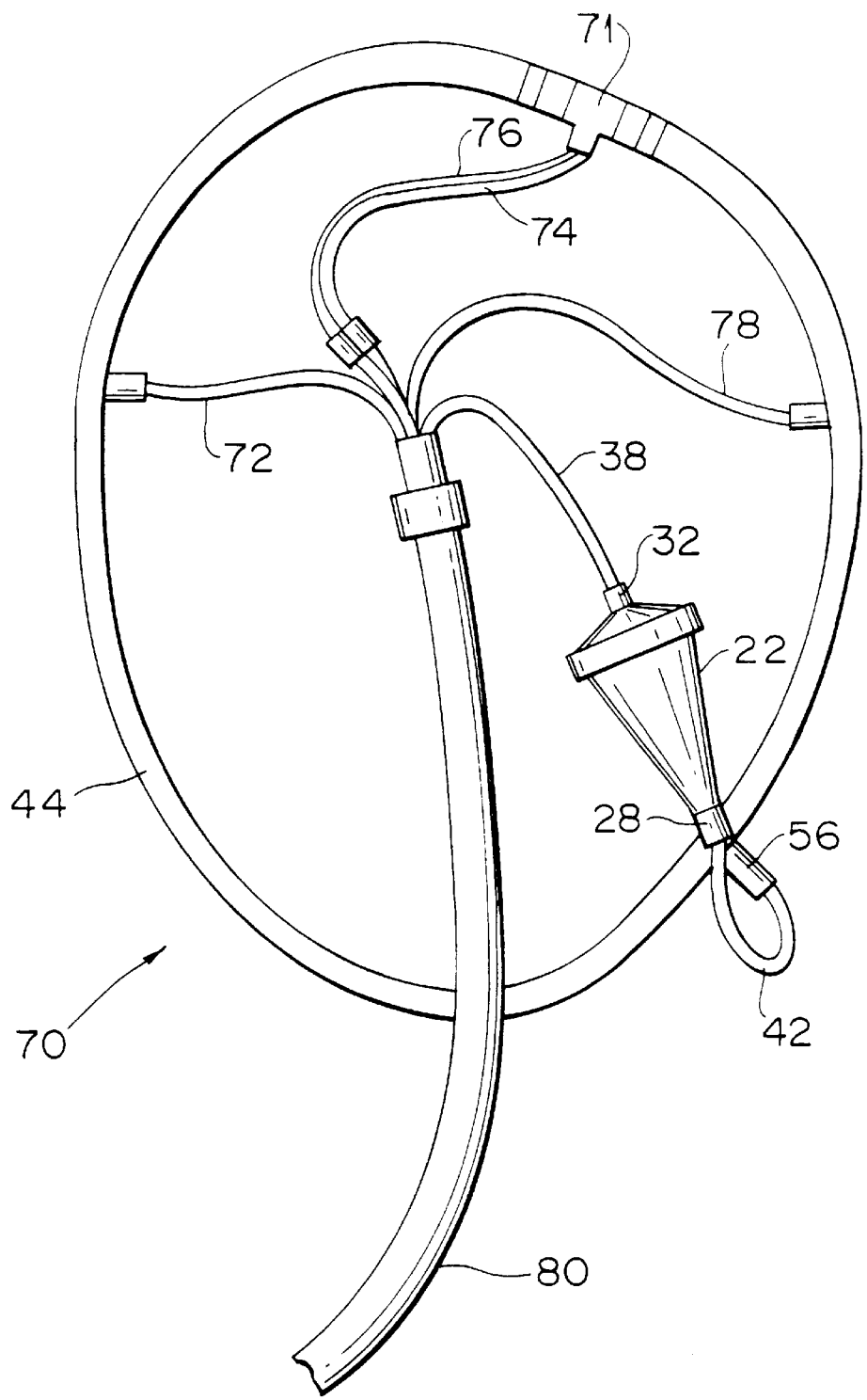
FIG. 4 depicts a portion of a tubing set in accordance with the invention.

As described above, the rotor 12 is configured with an annular passageway 14 that is open along a top surface as illustrated in FIG. 1. This passageway 14 is provided to receive a channel 44 of tubing set 70, as partially shown in FIG. 5. As best illustrated in FIG. 4, tubing set 70 preferably includes a semi-rigid conduit formed into a channel 44 having a generally rectangular cross-section. A connector 71 joins ends of the channel 44 to form an annular or loop shape that fits within passageway 14. A supply line 78 provides whole blood to an inlet of the semi-rigid channel 44, while a tubing segment 42, outlet lines 72, 74, and a control line 76 allow for removal of blood components during a centrifuge operation and flow control within the channel 44. Further details of the general configuration and functioning of the channel 44, tubing segment 42, and lines 72, 74, 76 and 78 are described in U.S. Pat. No. 4,708,712.

A protective sheath 80 surrounds the lines 72, 74, 76, 78 and outflow tubing 38. When the channel 44 of the tubing set 70 is removably positioned within the passageway 14, the lines 72, 74, 76 and 78 extend through slots 82, 84, 86, respectively, formed in wall 15, while the inflow tubing 42 rests in a slot 88 formed by passageway 14 (See FIGS. 1 and 5).

Figure 15:
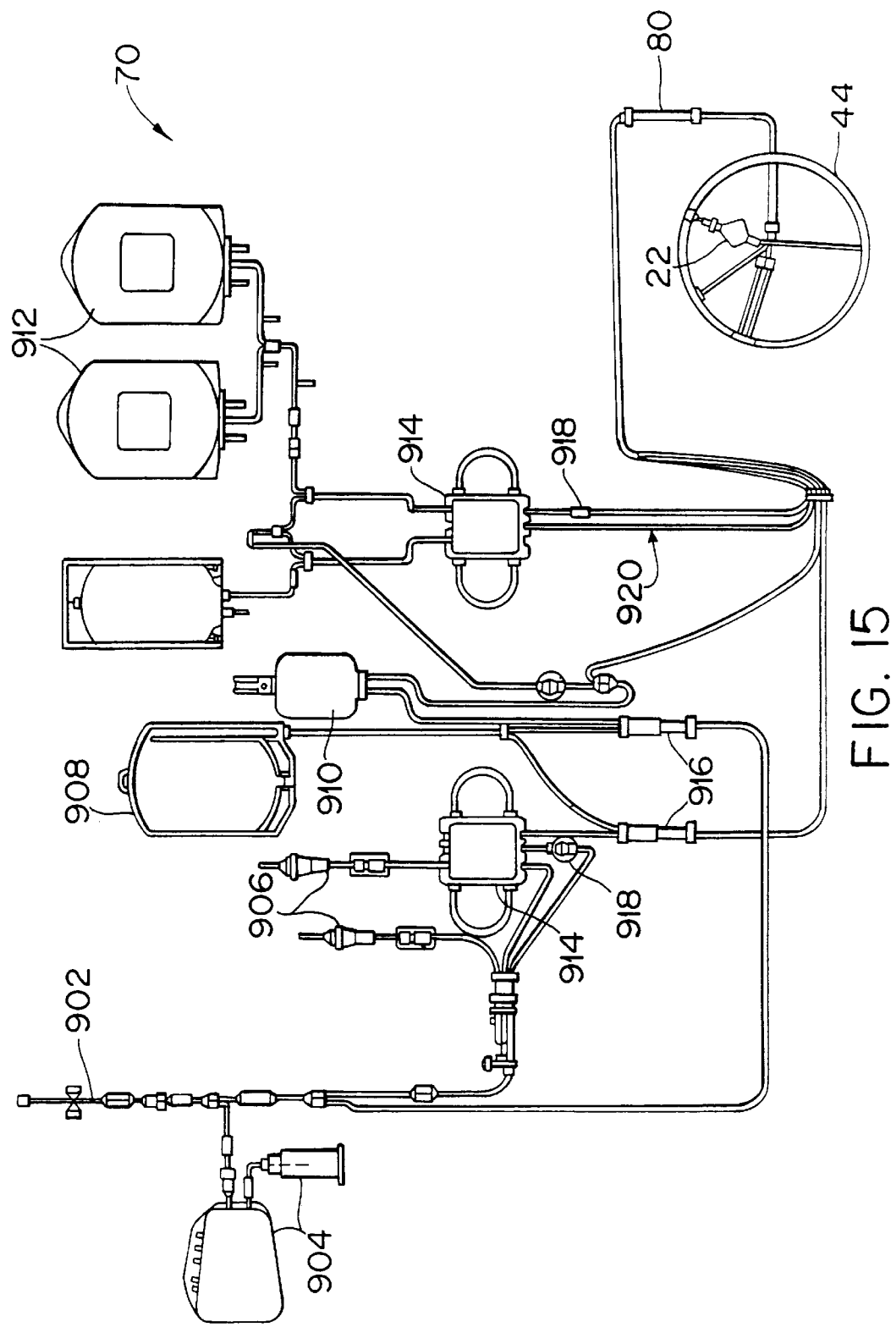
FIG. 15 is a schematic diagram illustrating a tubing set in accordance with the present invention, including the portion depicted in FIG. 4.

FIG. 15 is a more complete view of a second embodiment of the tubing set 70. The tubing set 70 may further include a plurality of additional elements for collecting blood components including, but not limited to one or more donor access lines 902, sample devices 904, spikes 906, filled solution bags (not shown) for the addition of fluids to the tubing set 70, wastes bags 908, accumulator bags 910, blood component bags 912, pump cartridges 914 for interfitting with various fluid pumps such as the pump 36, air chambers 916, monitoring device interfaces 918, interconnecting tubing and fittings 920, and various miscellaneous elements and accessories.

Figure 5:
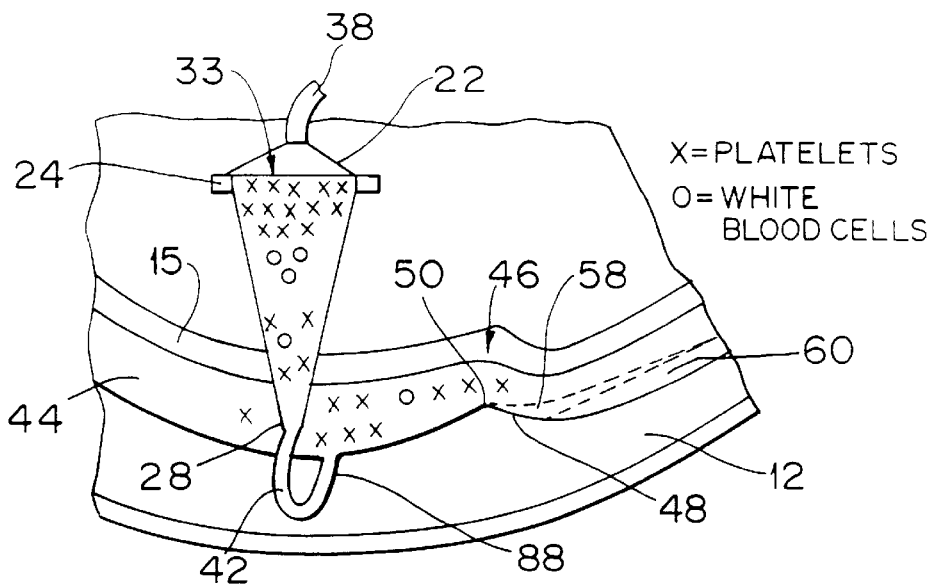
FIG. 5 schematically illustrates a saturated fluidized bed formed within a fluid chamber, where the fluid chamber is a component of the tubing set of FIG. 4 mounted to the centrifuge apparatus of FIG. 1.

As shown in FIGS. 3 and 5, a separation chamber 46 is positioned within a flow passage of the channel 44. Particles initially separate within the separation chamber 46 according to density and/or sedimentation velocity in response to centrifugal force. The separation chamber 46 includes a ridge 48 positioned on an outer wall of the passageway 14 for deforming a portion of the channel 44 to create a dam 50 within the channel 44. Alternatively, the dam 50 may be a permanent structure mounted within the flow passage of the channel 44. Although only a single separation chamber 46 and dam 50 are depicted in the figures, the flow passage may have multiple separation chambers or dams depending upon desired use.

When channel 44 is positioned in passageway 14, a collect well 54 forms in channel 44 adjacent dam 50. A tubing segment 42 connecting an outlet 56 of the well 54 to the inlet 28 of the fluid chamber 22 allows for separated substances in the collect well 54 to be conveyed to the fluid chamber 22. Although the embodiment shown in FIGS. 3–5 includes a tubing segment 42, any fluid coupling may be used between the separation chamber 46 and fluid chamber 22. For example, the inlet 28 of fluid chamber 22 may be directly connected to channel 44.

A method of separating particles of blood is discussed below with reference to FIGS. 3 and 5. Although the invention is described in connection with a blood component separation process, it should be understood that the invention in its broadest sense is not so limited. The invention may be used to separate a number of different particles. In addition the invention is applicable to both double needle and single needle blood purification or filtration applications. For example, the invention of the present application may be practiced with the SINGLE NEEDLE RECIRCULATION SYSTEM FOR HARVESTING BLOOD COMPONENTS of U.S. Pat. No. 5,437,624, issued Aug. 1, 1995, the disclosure of which is incorporated herein by reference.

Preferably the fluid chamber 22 is initially primed with a low density fluid medium, such as air, saline solution, or plasma, having a density less than or equal to the density of liquid plasma. This priming fluid allows for efficient establishment of a saturated fluidized bed of platelets within the fluid chamber 22. When a saline solution is used, this liquid enters the channel 44 through supply line 78. The saline then flows into the outlet 56 and through the chamber 22 when controller 40 activates pump 36. Controller 40 also initiates operation of the motor 16 to rotate the centrifuge rotor 12 and fluid chamber 22 in the direction of arrow "B" in FIG. 3. During rotation, twisting of fluid lines 72, 74, 76, 78 and outflow tubing 38 connected to the centrifuge rotor 12 and fluid chamber 22 is prevented by a sealless one-omega/two-omega tubing connection as is known in the art and described in U.S. Pat. No. 4,425,112.

After the apparatus is primed, and as the centrifuge rotates, whole blood or blood components are introduced through supply line 78 into the semi-rigid channel 44. When whole blood is used, the whole blood can be added to the semi-rigid channel 44 by transferring the blood directly from a donor through supply line 78. In the alternative, the blood may be transferred from a container, such as a blood bag, to supply line 78.

The blood within the channel 44 is subjected to a centrifugal force as the centrifuge rotor 12 continues to rotate in the direction of arrow "B" in FIG. 3. This centrifugal force acts in a radial direction away from the axis of rotation 13 of the rotor 12 as indicated by arrow "C" in FIG. 3.

The blood components undergo an initial separation within the channel 44. The components of whole blood stratify in order of decreasing density as follows: 1. red blood cells, 2. white blood cells, 3. platelets, and 4. plasma. The controller 40 regulates the rotational speed of the centrifuge rotor 12 to ensure that this particle stratification takes place. The blood particles form a buffy coat layer 58 and an outer layer 60 along an outer wall surface of the channel 44 within the separation chamber 46. The outer layer 60 includes particles having a density greater than the density of the particles in the buffy coat layer 58. Typically, the outer layer 60 includes red blood cells and white blood cells, while the buffy coat layer 58 includes platelets and white blood cells.

Plasma, the least dense blood component, flows within the channel 44 along the top surface of the buffy coat layer 58. When the height of the buffy coat layer 58 approaches the top of dam 50, the flowing plasma washes the platelets and some white blood cells of the buffy layer 58 over the dam 50. After these particles are washed over the dam 50, they enter the collect well 54. Some of the platelets may also flow past the collect well 54 and then reverse direction to settle back into the collect well 54, as described in U.S. patent application Ser. No. 08/422,598 entitled SPILLOVER COLLECTION OF SPARSE COMPONENTS SUCH AS MONONUCLEAR COMPONENTS OF WHOLE BLOOD, filed Apr. 14, 1995, the disclosure of which is incorporated herein by reference.

The white blood cells and red blood cells within the outer layer 60 are removed through outlet line 74, while platelet poor plasma is removed through outlet line 72. The controller 40 may control optional pumps (not shown) connected to lines 72, 74, or 76 to remove these blood components, as is known in the art. After the red blood cells, white blood cells, and plasma are thus removed, they are collected and recombined with other blood components or further separated. Alternately, these removed blood components may be reinfused into a donor.

Plasma carries platelets and white blood cells from the collect well 54 into the fluid chamber 22, filled with the priming fluid, so that a saturated fluidized particle bed may be formed. The controller 40 maintains the rotation speed of the rotor 12 within a predetermined rotational speed range to facilitate formation of this saturated fluidized bed. In addition, the controller 40 regulates the pump 36 to convey plasma, platelets, and white blood cells at a predetermined flow rate through the tubing segment 42 and into inlet 28 of the fluid chamber 22. These flowing blood components displace the priming fluid from the fluid chamber 22.

When the platelet and white blood cell particles enter the fluid chamber 22, they are subjected to two opposing forces. Plasma flowing through the fluid chamber with the aid of pump 36 establishes a first viscous drag force when plasma flowing through the fluid chamber 22 urges the particles toward the outlet 32 in the direction "D", shown in FIG. 3. A second centrifugal force created by rotation of the rotor 12 and fluid chamber 22 acts in the direction "C" to urge the particles toward the inlet 28.

The controller 40 regulates the rotational speed of the rotor 12 and the flow rate of the pump 36 to collect platelets and white blood cells in the fluid chamber 22. As plasma flows through the fluid chamber 22, the flow velocity of the plasma decreases as the plasma flow approaches the maximum cross-sectional area 33. This flow reaches a minimum velocity at this maximum cross-sectional area 33. Because the rotating centrifuge rotor 12 creates a sufficient gravitational field in the fluid chamber 22, the platelets accumulate near the maximum cross-sectional area 33 rather than flowing from the fluid chamber 22 with the plasma. The white blood cells accumulate somewhat below the maximum cross-sectional area 33. However, density inversion tends to mix these particles slightly during this initial establishment of the saturated fluidized particle bed.

The larger white blood cells accumulate closer to inlet 28 than the smaller platelet cells, because of their different sedimentation velocities. Preferably, the rotational speed and flow rate are controlled so that very few platelets and white blood cells flow from the fluid chamber 22 during formation of the saturated fluidized particle bed.

The platelets and white blood cells continue to accumulate in the fluid chamber 22 while plasma flows through the fluid chamber 22. As the concentration of platelets increases, the interstices between the particles become reduced and the viscous drag force from the plasma flow gradually increases. Eventually the platelet bed becomes a saturated fluidized particle bed within the fluid chamber 22. Since the bed is now saturated with platelets, for each new platelet that enters the saturated bed in the fluid chamber 22, a single platelet must exit the bed. Thus, the bed operates at a steady state condition with platelets exiting the bed at a rate equal to the rate additional platelets enter the bed after flowing through inlet 28. This bed is depicted schematically in FIG. 5, where the "X" symbol represents platelets and the "O" symbol represents white blood cells. As explained below, and depicted in FIG. 5, the saturated fluidized particle bed substantially obstructs or prevents white blood cells, "O", from passing through the fluid chamber 22.

The saturated bed establishes itself automatically, independent of the concentration of particles flowing into the fluid chamber 22. Plasma flowing into the fluid chamber 22 passes through the platelet bed both before and after the platelet saturation point.

The saturated bed of platelets occupies a varying volume in the fluid chamber 22 near the maximum cross-sectional area 33, depending on the flow rate and centrifugal field. The number of platelets in the saturated bed depends on a number of factors, such as the flow rate into the fluid chamber 22, the volume of the fluid chamber 22 and rotational speed. If these variables remain constant, the number of platelets in the saturated fluidized bed remains substantially constant. When the flow rate of blood components into the fluid chamber 22 changes, the bed self adjusts to maintain itself by either releasing excess platelets or accepting additional platelets flowing into the fluid chamber 22. For example, when the plasma flow rate into the fluid chamber 22 increases, this additional plasma flow sweeps excess platelets out of the now super-saturated bed, and the bed reestablishes itself in the saturated condition at the increased flow rate. Therefore, the concentration of platelets in the bed is lower due to the release of bed platelets.

After the saturated fluidized bed of platelets forms, flowing plasma carries additional platelets into the fluid chamber 22 and the bed. These additional platelets add to the bed and increase the viscous drag of the plasma flow through the bed. At some point the viscous drag is sufficient to cause platelets near the maximum cross-section area 33 to exit the saturated bed and fluid chamber 22. Thus, if the rotational speed and flow rate into the fluid chamber 22 remain constant, the number and concentration of platelets flowing into the saturated fluidized bed of platelets substantially equals the number and concentration of platelets released from the bed. This is in sharp contrast from the prior art.

Although the bed is saturated with platelets, a small number of white blood cells may be interspersed in the platelet bed. These white blood cells, however will tend to "fall" or settle out of the platelet bed toward inlet 28 due to their higher sedimentation velocity. Most white blood cells generally collect within the fluid chamber 22 between the saturated platelet bed and the inlet 28, as depicted in FIG. 5 and described below.

The saturated fluidized bed of platelet particles functions as a filter or barrier to white blood cells flowing into the fluid chamber 22. When blood components flow into the fluid chamber 22, plasma freely passes through the bed. However, the saturated fluidized platelet bed creates a substantial barrier to white blood cells entering the fluid chamber 22 an retains these white blood cells within the fluid chamber 22. Thus, the bed effectively filters white blood cells from the blood components continuously entering the fluid chamber 22, while allowing plasma and platelets released from the saturated bed to exit the chamber 22. This replenishment and release of platelets is referred to a the bed's self-selecting quality. Substantially all of these filtered white blood cells accumulate within the fluid chamber 22 between the saturated fluidized platelet bed and the inlet 28.

The particle separation or filtration of the saturated fluidized particle bed obviates a number of limitations associated with prior art elutriation. For example, particles may be separated or filtered in a continuous steady state manner without batch processing. In addition, an additional elutriating fluid medium is not required. Furthermore, after the saturated fluidized particle bed is established, flow rates may be varied over a range without changing the size of the particles leaving the fluid chamber 22. Unlike prior art elutriation, the present invention establishes a saturated particle bed consisting of numerically predominant particles. This bed automatically passes the predominant particles while rejecting larger particles.

The apparatus and method of the invention separate substantially all of the white blood cells from the platelets and plasma flowing through the fluid chamber 22. The barrier to white blood cells is created, at least in part, because white blood cells have a size and sedimentation velocity greater than that of the platelets forming the saturated fluidized particle bed. Therefore, particles of similar densities are separated according to different sizes or sedimentation velocities.

Because the initial separation at dam 50 and the saturated fluidized bed remove a majority of the red blood cells and white blood cells, the fluid exiting the fluid chamber 22 consists mainly of plasma and platelets. A device as described herein was operated 30 times using whole human blood. Each operation resulted in a leukopoor product having less than $3 \times 10^6$ white blood cells per $3 \times 10^{11}$ platelets. Based on these results it is expected that platelet product exiting the fluid chamber 22 will consistently (at least 99% of the time) meet the leukopoor standard of less than $5 \times 10^6$ white blood cells when at least $3 \times 10^{11}$ platelets flow from the fluid chamber 22.

Unlike a conventional porous filter, where the filtered white blood cells are retained in the filter, the present invention allows a substantial fraction of white blood cells to be recovered and returned to the donor.

Preferably, 80% to 99% of the platelets initially entering the channel 44 may be recovered in a viable state. More preferably, at least 95% or at least 98% of the platelets initially entering the channel 44 are recovered from both the channel 44 and the fluid chamber 22.

When the blood components are initially separated with the separation chamber 46, a substantial number of platelets may become slightly activated. The saturated fluidized platelet bed allows white blood cells to be filtered from plasma and platelets despite this slight activation. Thus, the present invention does not require a waiting period to filter white blood cells after blood components undergo initial separation in a separation chamber 46. This is in contrast to methods using conventional filters.

After separation, the platelets and plasma exiting the fluid chamber 22 are collected in appropriate containers and stored for later use. The red blood cells and white blood cells removed from the semi-rigid channel 44 may be combined with the remainder of the plasma in the system for donor reinfusion or storage. Alternatively, these components may be further separated by the apparatus 10.

In an embodiment of the invention, the controller 40 regulates the rotational speed of the rotor 12 within a preferred range of 1,800 to 2,400 RPM. Preferably the rotation is controlled at 2,400 RPM to create a gravitational field within the fluid chamber 22 ranging from approximately 800G adjacent to the inlet 28 to approximately 500G adjacent to the outlet 32. The controller 40 maintains the flow rate into the fluid chamber 22 within a range of 1 ml/min to 15 ml/min. The preferred flow rate ranges from 2 ml/min to 8 ml/min. The specific flow rate is selected according to an initial platelet count and the total volume of whole blood being processed, among other things.

In an embodiment of the invention, filtering may take place at the same flow rate used to form the saturated fluidized bed. Optionally the flow rate during filtering may be greater than the flow rate used during the bed formation to increase the rate of particle filtration. For this optional arrangement, the controller 40 may increase the flow rate of the blood components entering the fluid chamber 22 while maintaining the saturated fluidized bed. The controller 40 increases flow rate by increasing the rate of pump 36.

The controller 40 maintains the saturated fluidized bed throughout the filtering process as blood components flow into the fluid chamber 22. The controller 40 ensures that the flow through the fluid chamber 22 is smooth and steady by regulating the supply of fluid and rotation of the centrifuge rotor 12. This regulation properly balances the forces in the fluid chamber 22 to maintain the saturated fluidized bed. As described in more detail below, the controller 40 may increase flow into the fluid chamber 22 while maintaining the saturated fluidized bed.

At the end of a blood component separation session, the controller 40 may recover platelets retained both in the buffy coat layer 58 of channel 44 and within the saturated fluidized bed of fluid chamber 22. The controller 40 recovers platelets in the buffy coat layer 58 by either decreasing rotational speed of the rotor 12 or increasing the amount of plasma exiting the channel 44. For example, in a preferred manner of recovering platelets in the buffy coat layer, the rotor speed is suddenly decreased from 2,400 RPM to 1,800 RPM, and then increased back to 2,400 RPM. This spills platelets and white blood cells retained in the buffy coat layer 58 over the dam 50 and into the fluid chamber 22. Within the fluid chamber 22 the saturated fluidized platelet bed blocks passage of the white blood cells from the buffy coat layer 58, while buffy coat layer 58 platelets simultaneously add to the bed and release platelets from the saturated bed. Thus, the apparatus may filter substantially all of the white blood cells from the buffy coat layer 58. This increases platelet yield significantly.

The buffy coat layer 58 may spill over the dam in the manner described in above-mentioned U.S. patent application Ser. No. 08/422,598. This is particularly effective in a mononuclear cell collection procedure, because the fluid chamber 22 may allow for separation of red blood cells from mononuclear cells.

In addition, platelets in the saturated fluidized bed are harvested to recover a substantial number of platelets from the fluid chamber 22. During bed harvest, the controller 40 increases the flow rate and/or decreases the centrifuge rotor 12 speed to release platelets from the bed. This flushes from the fluid chamber 22 most of the platelets that made up the saturated fluidized bed to substantially increase platelet yield. The harvesting continues until substantially all of the platelets are removed, just before an unacceptable number of white blood cells begin to flow from the fluid chamber 22.

The harvested platelets that made up the bed may be combined with the platelets previously collected. In addition, the remainder of contents of the fluid chamber 22, having a high concentration of white blood cells, can be separately collected for later use or recombined with the blood components removed from channel 44 for return to a donor.

The invention particularly allows trace or contaminating first particles to be separated from a liquid having a larger number of second particles. Preferably the first particles to be filtered, such as white blood cells, have a concentration insufficient to form a saturated fluidized particle bed. However, the invention in its broadest application is directed to either separating first particles from liquid or separating first from second particles without concern for particular particle concentrations.

Although the inventive device and method have been described in terms of removing white blood cells and collecting platelets, this description is not to be construed as a limitation on the scope of the invention. The invention may be used to separate any of the particle components of blood from one another. For example, the saturated fluidized bed may be formed from red blood cells to prevent flow of white blood cells through the fluid chamber 22, so long as the red blood cells do not rouleau (clump). Alternatively, the liquid for carrying the particles may be saline or another substitute for plasma. In addition, the invention may be practiced to remove white blood cells or other components from whole blood removed from an umbilical cord to collect stem cells. Further, one could practice the invention by filtering or separating particles from fluid unrelated to either blood or biologically related substances.

The apparatus and method of the invention may separate white blood cells, including stem cells, and tumor cells by forming a saturated fluidized particle bed of stem cells to substantially prevent tumor cells from flowing through the fluid chamber 22. In the alternative, the tumor cells may form a saturated fluidized particle bed to substantially obstruct flow of stem cells through the fluid chamber 22.

In another aspect of the invention, smaller first particles, such as tumor cells, may be separated from larger second particles, such as stem cells, by forming a saturated fluidized particle bed with intermediate sized third particles. Initially, intermediate sized third particles are added to a liquid carrying the first and second particles. Preferably, the concentration of added third particles exceeds the concentration of both the first and second particles. These third particles are preferably magnetic micro-beads or some other substance readily separable from the other particles.

The liquid carrying the first, second, and third particles then passes into the fluid chamber 22. Eventually, the third particles form a saturated fluidized particle bed, in the same manner as described above. As more of the liquid and particles flow into the fluid chamber 22, the liquid an smaller first particles pass through the saturated third particle bed, while the bed and particle sedimentation characteristics obstruct movement of the second particles through the bed. Thus, the first and second particles separate within the fluid chamber 22.

The saturated fluidized bed may release third particles as more third particles flow into the bed or when flow rate into the fluid chamber 22 changes. These third particles may be removed from the liquid and first particles exiting the fluid chamber 22. In a preferred embodiment, a particle remover (not shown) having a magnet, magnetically attracts magnetic third particles to remove them from the liquid. Thus, a substantially purified concentration of first particles is obtained.

This alternate method is useful to separate first and second particles both being present in low concentrations and having similar densities, but different sizes. Although the third particles for forming the bed are preferably added along with the first and second particles, they may also be introduced into the fluid chamber 22 in separate steps. This aspect of the invention may be particularly useful in separating tumor cells from stem cells or other blood components, as mentioned above. Alternatively, the first particles may be T cells and the second particles may be stem cells. However, this variant of the inventive method may be practiced to separate many different types of particles. For example, T cells can be separated from stem cells so as to reduce graft versus host disease after stem cell transfusion.

Additional embodiments of the invention will now be described where like or similar elements are identified throughout the drawings by reference characters having the same final two digits.

Figures 6, 7:
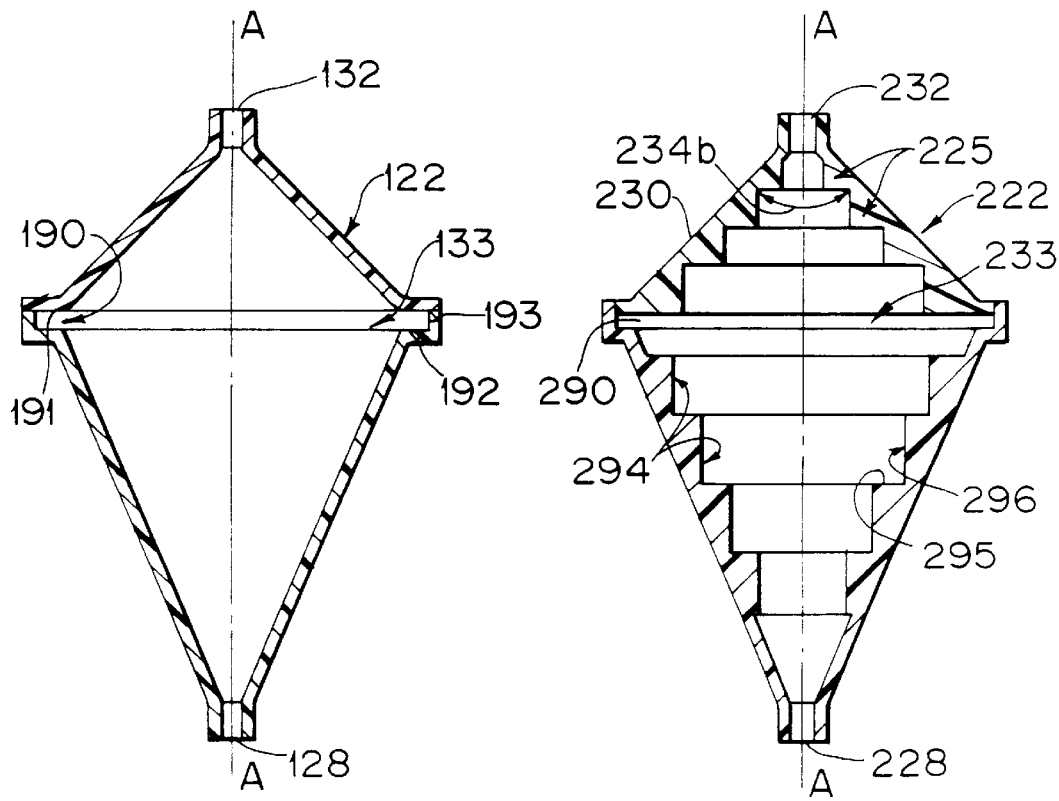
FIG. 6 is a cross-sectional view of a first alternate embodiment of the fluid chamber of FIG. 2.
FIG. 7 is a cross-sectional view of a second alternative embodiment of the fluid chamber of FIG. 2.

As shown in FIG. 6, another embodiment of the invention includes a fluid chamber 122 having an inlet 128 and an outlet 132. A groove 190 is formed on an inner surface of the fluid chamber 122 at a position of the maximum cross-sectional area 133. Top and bottom portions 191, 192, oriented substantially perpendicular to a longitudinal axis A—A of the fluid chamber 122, are joined by a side 193. Preferably, the side 193 is parallel to the axis A—A and surrounds this axis to form the substantially annular groove 190.

In an embodiment of the invention, the side 193 is 0.1 inches, while the top and bottom portions 191, 192 are each 0.08 inches. However, the groove 190 may be configured in many different shapes and sizes without departing from the invention.

The groove 190 helps to disperse Coriolis jetting within the fluid chamber 122. Thus, groove 190 improves the particle barrier capability of the saturated fluidized particle bed. Sudden increases in liquid flow rate during a particle separation procedure may limit the ability of the saturated fluidized particle bed to obstruct particle passage. Liquid flowing into the fluid chamber 22 undergoes a Coriolis jetting effect. This jetting flow reduces the filtration effectiveness of the saturated fluidized particle bed because liquid and particles may pass between the saturated fluidized particle bed and an interior wall surface of the fluid chamber 22 rather than into the bed itself. The fluid chamber 122 including groove 190 counteracts these effects by channeling Coriolis jetting flow in a circumferential direction partially around the axis A—A of fluid chamber 122. Therefore, the groove 190 improves the particle obstruction capability of the saturated bed, especially when liquid flow rates increase.

FIGS. 16 and 17 depict fluid chambers 1022 and 1022', respectively, having alternate embodiments of grooves 1090, 1090'. As illustrated in FIG. 16, fluid chamber 1022 includes a groove 1090 having a side 1093 and top and bottom portions 1091 and 1092 formed circumferentially on the inner side of the fluid chamber 1022 at a position of a maximum cross-sectional area 1033. These top and bottom portions 1091 and 1092 may be perpendicular to a longitudinal axis A—A, while the side 1093 may be parallel to the axis A—A to form a substantially annular groove 1090.

As shown in FIG. 16, a circumferential lip 1094, located closer to the axis A—A than the side 1093, extends from the top portion 1091. The bottom portion 1092 and lip 1094 define a groove entrance 1096. As shown in FIG. 16, this groove entrance 1096 may completely surround axis A—A.

Alternatively, as shown in FIG. 17, the groove entrance may include a plurality of slot-shaped entrances 1095' spaced about the circumference of the fluid chamber 1022' at the position of maximum cross-sectional area 1033'. In this embodiment, the lip 1094' extends to the bottom portion 1092' to form an inner groove wall 1097' located between the slot-shaped entrances 1095.

Preferably, a first entrance 1095' may be provided at a location corresponding to the location of Coriolis jetting, and a second entrance (not shown) may be provided at a diametrically opposite location. The Coriolis jet flow enters the groove 1090' at a first slot-shaped entrance 1095', travels circumferentially around the groove 1090' in both clockwise and counter-clockwise directions, and then exits at another slot-shaped opening.

The configurations of FIGS. 16 and 17 are believed to improve direction of Coriolis jetting momentum and further improve performance. The groove configurations of FIGS. 16 and 17 may be optionally employed in conjunction with any of the fluid chamber embodiments described herein.

FIG. 7 depicts another embodiment of a fluid chamber 222. A plurality of steps 294 are formed on an inner surface of the fluid chamber 222 between the position of the maximum cross section 233 and the inlet 228. Although only four steps 294 are illustrated, any number of steps 294 may be provided in the fluid chamber 222.

Each step 294 has a base surface 295 oriented substantially perpendicular to a longitudinal fluid chamber axis A—A. In addition, a side surface 296 is positioned orthogonal to the base surface 295. Although FIG. 7 depicts a corner where side surface 295 and base surface 295 interact, a concave groove may replace this corner. In a preferred embodiment each step 294 surrounds the axis A—A to bound a cylindrical shaped area. Further, the fluid chamber 222 optionally includes a groove 290.

The base surface 295 is 0.05 inches and the side surface 296 is 0.02 inches in a preferred embodiment. However, the sizes for these surfaces and the configuration of each step 294 may be modified without departing from the scope or spirit of the invention.

Adding steps 294 to the fluid chamber 222, also improves the particle obstruction characteristics of the saturated fluidized particles bed, in particular during increases in the rate of fluid flow. The steps 294 provide this improvement by providing momentum deflecting and redirecting surfaces to reduce Coriolis jetting in fluid chamber 222. When Coriolis jetting takes place, the liquid and particles of the jet travel along an interior surface of the fluid chamber 222 that faces the direction of centrifuge rotation. Therefore, the jet may transport particles between the fluid chamber interior surface and either a saturated fluidized particle bed or an elutriation field positioned in the fluid chamber 222. Thus, particles traveling in the jet may exit the fluid chamber 222 without being separated.

Steps 294 direct or alter the momentum of the Coriolis jet flow of liquid and particles generally in a circumferential direction about axis A—A. Thus, a substantial number of particles originally flowing in the jet must enter the saturated fluidized bed or elutriation field to be separated.

As shown in FIG. 7, the fluid chamber 222 may include additional steps 225 shaped similar to steps 294. The additional steps 225 are located between the position of the maximum cross-section 233 and a fluid chamber outlet 232. In a fashion similar to that described above, these steps 225 tend to redirect the Coriolis jet flow in a circumferential direction surrounding axis A—A.

In addition to adding steps 294 and 225, the conical angle 234b of the second chamber 230 may be decreased from 120° to 45° to reduce particle contamination caused by density inversion. If faster sedimenting particles should migrate past the maximum cross section 233, the smaller angled walls partially limit some of these particles from flowing directly to outlet 232 because density inversion does not exist in the section 230. Thus, the faster sedimenting particles will "fall" or migrate back between area 233 and inlet 228 under the influence of the gravity centrifugal field, rather than flowing from outlet 232. Optionally, any of the fluid chambers disclosed herein may include a second chamber section 230 with a conical angle 234b less than 120°.

Figure 8:
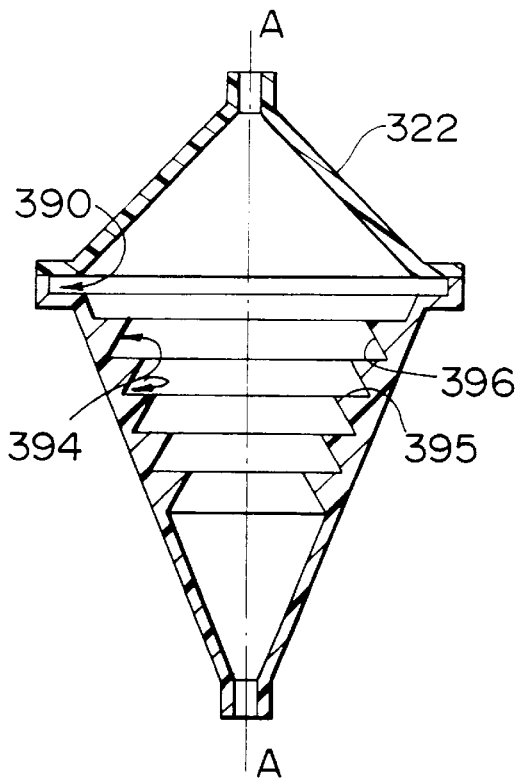
FIG. 8 is a cross-sectional view of a third alternative embodiment of the fluid chamber of FIG. 2.

FIG. 8 illustrates an additional embodiment of a fluid chamber 322 having steps 394 and an optional groove 390 similar to groove 190. As shown in FIG. 8, each step 394 includes a base surface 395 substantially perpendicular to axis A—A. This embodiment also includes a side surface 396 oriented at an acute angle to the base surface 395.

Figure 9:
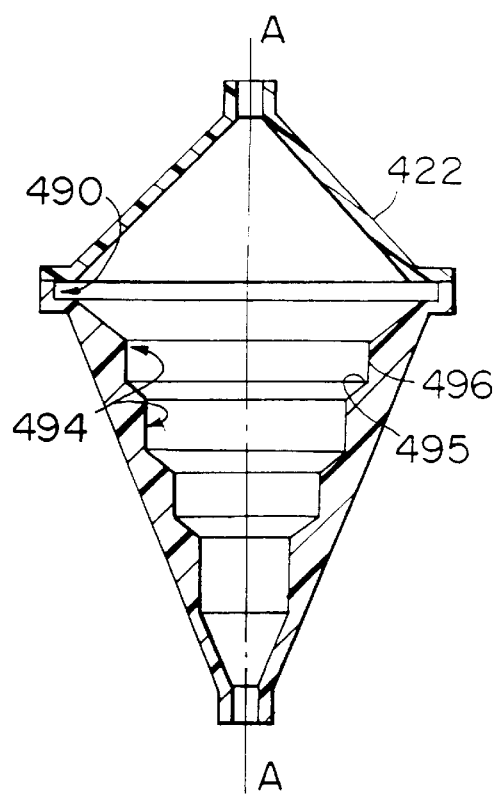
FIG. 9 is a cross-sectional view of a fourth alternative embodiment of the fluid chamber of FIG. 2.

In FIG. 9 a further embodiment of a fluid chamber 422 including flow limiting steps 494 and an optional groove 490 is depicted. A side surface 496 of each step 494 is substantially parallel to an axis A—A and forms an obtuse angle with base surface 495.

In FIGS. 6–9, the grooves 190, 290, 390, 490 and steps 294, 394, 494 may either completely or only partially surround the chamber axis A—A. These features are provided to facilitate fluid flow rate increases, as described below, as well as to improve steady state performance of the fluid chamber. During blood component separation, the grooves 190, 290, 390, 490 and steps 294, 394, 494 greatly reduce the number of white blood cells that would otherwise bypass the saturated fluidized platelet bed.

The grooves 190, 290, 390, 490, steps 294, 394, 494, and additional steps 225 may be formed in many different configurations without departing from the scope, or spirit of the invention. For example, the base surface and/or side surface of one or more of the steps 294, 394, 494 may have a concave shape. In addition the steps 294, 394, 494 may be arranged in a spiral surrounding axis A—A. Further, a portion of the base surface 295, 395, 495 extending around axis A—A may be positioned lower than a remainder of this surface to form a concavity.

Although the fluid chambers 122, 222, 322, 422, 1022, 1022' are described for use in forming a saturated fluidized particle bed, this description is not intended to limit the scope of the invention in its broadest sense. Because particle separation difficulties, such as those discussed in Sartory, may be reduced or eliminated, a significant advancement from the prior art has been made. These fluid chambers 122, 222, 322, 422 may be used in any particle separation process. In particular, a fluid chamber having a channel, step, or additional step may be used in elutriation.

The grooves 190, 290, 390, 490, steps 294, 394, 494, and additional step 225 may be formed in an injection molding process. Preferably, the fluid chambers 22, 122, 222, 322, 422, 1022, 1022' are initially formed by injection molding in multiple pieces, preferably two, and bonded together by any of several well known processes, such as RF welding, ultrasonic welding, hot plate welding, solvent bonding, or adhesive bonding. Alternatively, these fluid chambers may be formed from a unitary plastic material, as by blow molding. However, any known manufacturing process may be practiced to fabricate the chambers.

When one of the fluid chambers 122, 222, 322, 422, 1022, 1022' is substituted for the fluid chamber 22, the controller 40 may regulate flow of the liquid having first particles in number of preferred ways. Because these fluid chamber designs reduce Coriolis jetting and/or density inversion, the controller 40 may increase flow rate without disrupting the saturated fluidized particle bed.

While maintaining rotational speed of the rotor 12 at a substantially constant rate, the controller 40 may increase flow through the fluid chamber 122, 222, 322, 422, 1022, 1022' with one of, or a combination of, the following different routines. In one routine the controller 40 increases flow rate by rapidly or instantaneously increasing flow through the fluid chamber 122, 222, 322, 422, 1022, 1022'. In another routine, flow rate is increased gradually over time. In yet a further routine, the controller 40 increases flow rate in a sequential manner by gradually increasing the flow rate, maintaining this increased flow rate, and then gradually increasing flow rate again.

However, if the apparatus 10 includes the fluid chamber 22, shown in FIGS. 1–5, the flow rate control may be more limited. The flow velocity of the liquid and particles entering the fluid chamber 22 should not undergo rapid or extreme fluctuation, otherwise temporary disruption of the effectiveness of the bed may result. The flow velocity can drop suddenly without affecting the bed, however sudden increases in velocity, if large enough, may disrupt the bed to allow particles, such as white blood cells, to exit the fluid chamber 22.

The controller 40 increases flow into the fluid chamber 22 while maintaining the saturated fluidized bed. The controller 40 may perform this flow rate increase by gradually increasing flow in a continuous fashion until a final flow rate is achieved. In a preferred embodiment, including the fluid chamber 22 shown in FIG. 2, the controller 40 increases the flow rate into the fluid chamber 22 by a ratcheting process.

The controller 40 maintains the bed and increases the flow rate in the ratcheting process by initially reducing the rotational speed of the rotor 12. However, the rotational speed of the rotor 12 is not reduced to a level that allows red blood cells in outer layer 60 to spill over dam 50, otherwise a significant number of both red blood cells and white blood cells will flow into the fluid chamber 22. In an embodiment of the invention, the controller 40 lowers the rotational speed of the rotor 12 so that a centrifugal force at dam 50 remains above 850 G. Then, the controller calculates a value for $K=Q_i/N_i^2$, where K is a constant, $Q_i$ is the current flow rate into the fluid chamber 22, and $N_i$ is the current rotational speed of the centrifuge rotor 12.

After the controller 40 reduces the rotational speed of the rotor 12 and calculates K, the controller 40 simultaneously increases both the flow rate into the fluid chamber 22 and the rotational speed of the rotor 12. Thus, an increasing centrifugal force in the fluid chamber 22 counteracts with increasing fluid flow forces in the fluid chamber 22 to maintain the saturated fluidized particle bed as a barrier to other particles. The new flow rate into the chamber, Q, and the new rotational speed N satisfy the equation: $Q/N^2=K$. Therefore, $Q/N^2$ equals $Q_i/N_i^2$.

To increase the flow rate even further, the controller 40 may continue to simultaneously increase both flow rate and rotational speed. Also, if necessary, the controller 40 may repeat the ratcheting process to further increase flow rate. This is accomplished by repeating the steps of reducing rotational speed and simultaneously increasing both flow rate and rotational speed.

In addition, the controller 40 preferably returns the saturated fluidized particle bed to its original state if a pause in fluid flow to the fluid chamber 22 causes the bed to collapse. The controller 40 may constantly monitor both flow rate, Q, and rotational speed, N, to calculate a value for $K=Q/N^2$. If the flow into the fluid chamber 22 momentarily pauses to collapse the saturated fluidized bed, the particles that made up the bed temporarily remain in the fluid chamber 22. When fluid flow to the fluid chamber 22 is reinitiated, the controller 40 controls both the flow rate, Q, and rotational speed, N, so that these parameters satisfy the $K=Q/N^2$ relationship existing immediately before fluid flow to the fluid chamber 22 was interrupted. This automatically returns the particles of the collapsed bed back into a saturated fluidized bed form.

After a bed collapses the saturated fluidized particle bed may recover in many other different ways. For example, after a pause in fluid flow the flow rate may be increased in a stepwise or gradual fashion to provide bed recovery.

Figure 10:
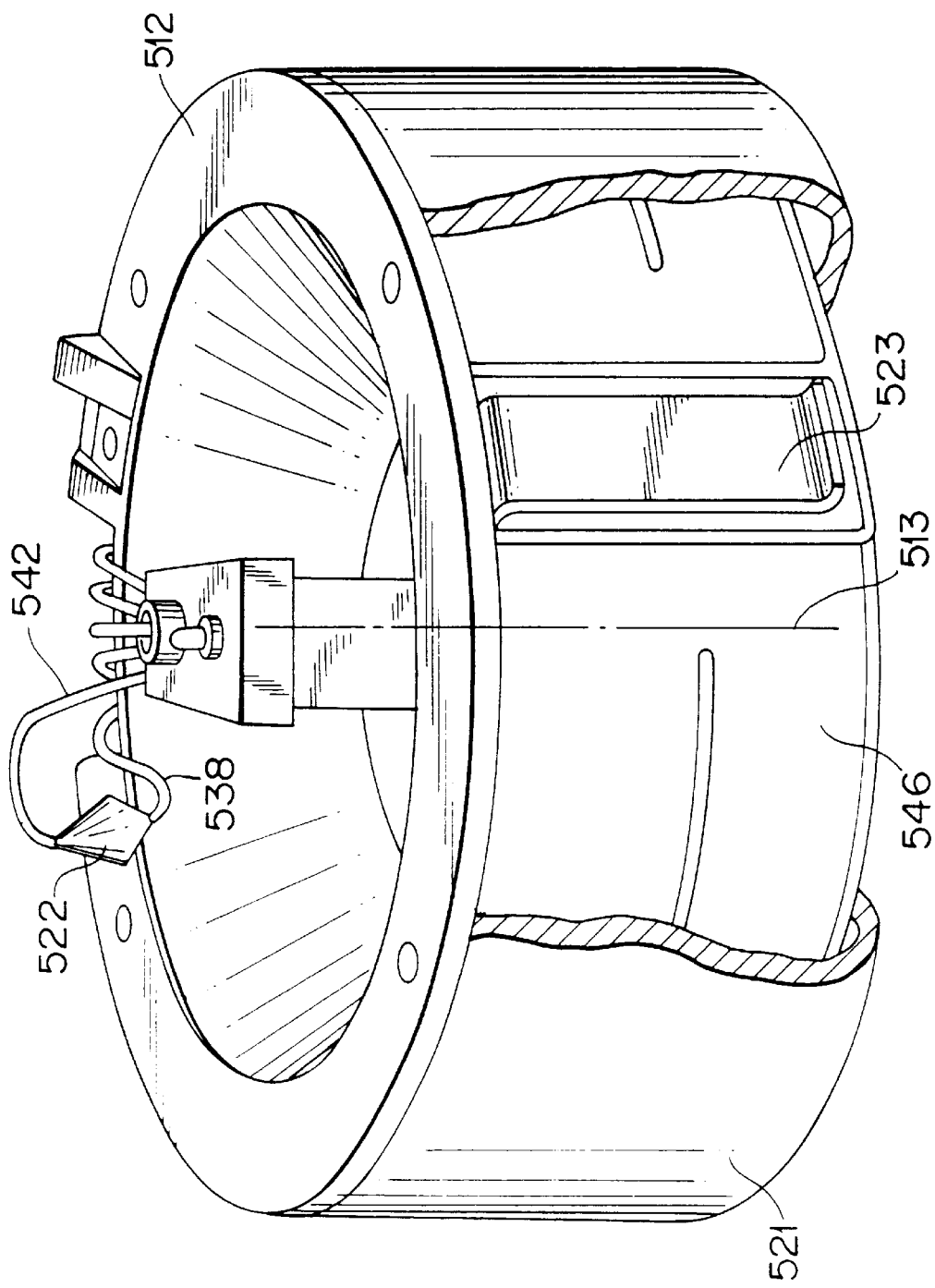
FIG. 10 is a perspective view of an alternate embodiment of a centrifuge apparatus of the invention.

FIG. 10 illustrates another embodiment of the invention. In this embodiment a fluid chamber 522 is mounted on a centrifuge rotor 512. The rotor 512 includes an outer bowl 521 and a clip 523 for holding a separation chamber 546 formed in an elongated flexible tubular or belt shape from plastic material. The device depicted in FIG. 10 separates particles, in particular blood components, within the separation chamber 546 by generating centrifugal force. For further details concerning the configuration and operation of this device, refer to U.S. Pat. No. 5,362,291 to Williamson, I. V., U.S. Pat. No. 5,360,542 to Brown et al., and U.S. Pat. No. 5,078,671 to Dennehey et al., the disclosures of which are incorporated herein by reference.

The fluid chamber 522 is mounted or held on the centrifuge rotor 512 with an outlet 532 facing substantially toward an axis of rotation 513 of the centrifuge rotor 512. Inflow tubing 542 supplies liquid and particles to the fluid chamber 522 after the particles undergo an initial separation within a portion of the separation chamber 546. In a similar fashion, outflow tubing 538 conveys substances from the fluid chamber 522 to another portion of the separation chamber 546.

In using the embodiment shown in FIG. 10, particles carried by a liquid are separated in the separation chamber 546 according to density and size differences of the particles. After being initially separated, the liquid and particles, for example plasma carrying platelets and white blood cells, flow into the fluid chamber 522. Within fluid chamber 522, a saturated fluidized particle bed forms to further separate particular particles from the flowing liquid.

Figure 11:
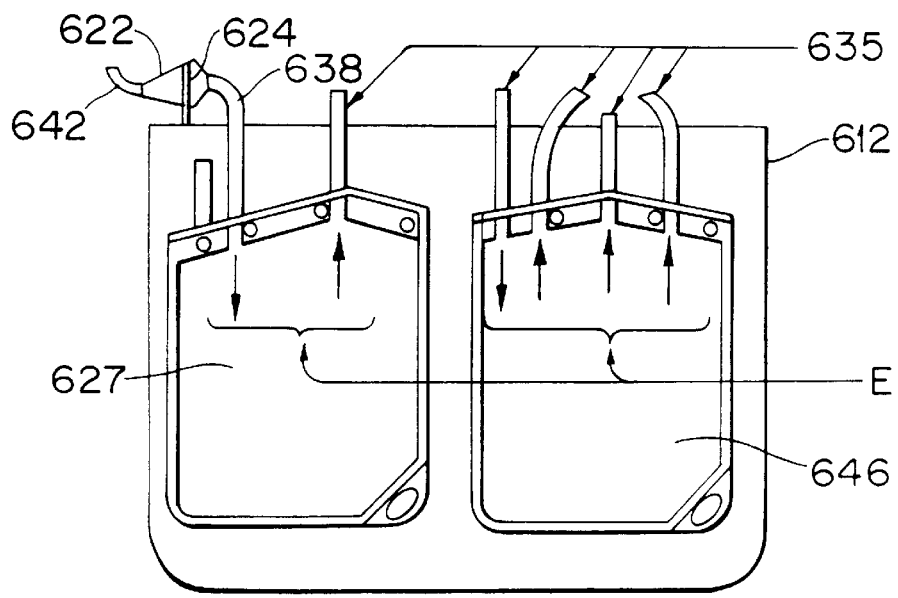
FIG. 11 is a cross-sectional schematic view of another embodiment of the centrifuge apparatus of the invention.
Figure 12:
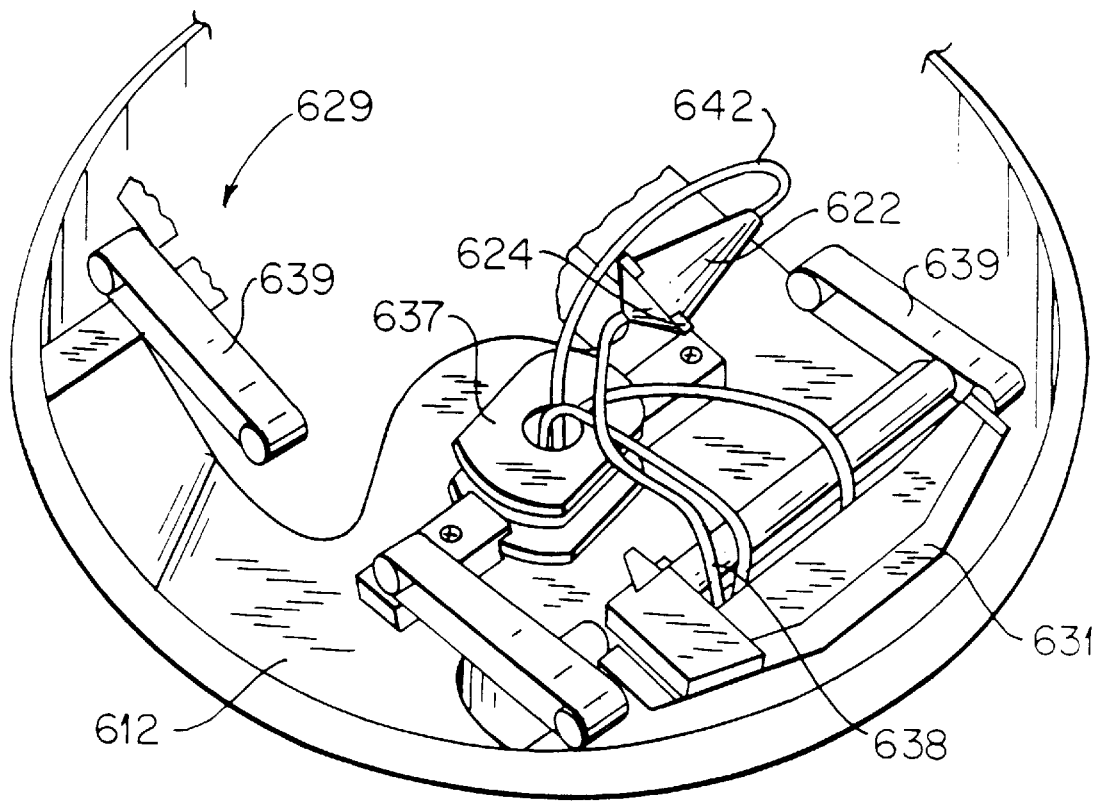
FIG. 12 is a partial perspective of the centrifuge apparatus of FIG. 11.

Yet another embodiment of the invention is illustrated in FIGS. 11 and 12. This embodiment includes both a separation chamber 646 shaped as a container and a collection container 627. Holders 629, 631 hold separation chamber 646 and container 627, respectively, on a centrifuge rotor 612. Flow lines 635, 638 provide fluid flow to and from the separation chamber 646 and container 627 as indicated by the arrows labelled with the symbol "E" shown in FIG. 11. Further components include a restraining collar 637 and container holder clamp assemblies 639. Particles are separated according to density and size differences within the separation chamber 646 in response to centrifugal force. For further details of how this device is configured and operates, refer to Baxter Heathcare Corporation's CS-3000® Plus Blood Separator Operator's Manual (7-19-3-136), the disclosure of which is incorporated herein by reference.

As depicted in FIGS. 11 and 12, a holder 624 holds a liquid chamber 622 on the rotor 612. Inflow tubing 642 conveys liquid and particles initially separated in separation chamber 646 into the fluid chamber 622. In addition, an outflow tubing 638 fluidly couples the fluid chamber 622 to the collection container 627. With this configuration, a saturated fluidized particle bed may be formed in the fluid chamber 622, as explained with respect to the above embodiments, to filter particles.

FIG. 13 illustrates a further embodiment of the invention. This embodiment includes a separation chamber 746, preferably formed from rigid transparent plastic conduit, capable of being inserted into a centrifuge. An inlet 741 allows whole blood to flow into a first stage 743 of the separation chamber 746, so that red blood cells may be removed from a conduit 745, while platelet rich plasma flows through conduit 742. In addition, a conduit 747 and outlet 749 enable removal of platelet poor plasma and platelets, respectively, in a second stage 751. For further details regarding the structural configuration and operation of this embodiment, refer to the Brief Operating Instructions of the Fresenius MT AS 104 blood cell separator (4/6.90(OP)), the disclosure of which is incorporated herein by reference.

As shown in FIG. 13, a fluid chamber 722 may be coupled to the separation chamber 746. A saturated fluidized particle bed may be formed in the fluid chamber 722 to separate particles after initial particle separation in the separation chamber 746, in the manner described above.

In an alternate embodiment (not shown), the fluid chamber 722 may be coupled to outlet 749 of second stage 751. This alternate embodiment would allow for particles to be separated in a manner similar to the particle separation described for the embodiment shown in FIGS. 1–5.

FIG. 14 illustrates yet another embodiment of the invention. As shown, a separation chamber 846 and a first fluid chamber 822a are provided on a centrifuge rotor 812 in a manner similar to that of the embodiment of FIGS. 1–5. In addition, an outflow tubing 838 fluidly couples an outlet 832a of the fluid chamber 822a to an inlet 828b of an auxiliary fluid chamber 822b. Mounting brackets (holders) 824a, 824b maintain the fluid chamber and the auxiliary chamber 822a, 822b, respectively, at substantially the same radial distance from a rotation axis of the centrifuge rotor 812.

In using the embodiment shown in FIG. 14, centrifuge rotor 812 rotates to initially separate particles within separation chamber 846 according to density and/or sedimentation velocity. Liquid carries separated particles into the first fluid chamber 822a where particles further separate after formation of a saturated fluidized bed of particles or an elutriation field. Thereafter, the separated particles and liquid flow through tubing 838 into auxiliary fluid chamber 822b where particles are further separated by either a saturated fluidized bed of particles or an elutriation field. Thus, particles separate within chambers 822a, 822b by forming a saturated fluidized particle bed in one of the chambers 822a, 822b and an elutriation boundary in another of the chambers 822a, 822b, or, in the alternative, by forming either a saturated fluidized particle bed or an elutriation boundary in both of the chambers 822a, 822b.

Optionally the chambers 822a, 822b may have different dimensions, such as differing volumes, lengths or maximum diameters. For example, fluid chamber 822a may have a greater volume than that of auxiliary chamber 822b. These different dimensions allow for two different particle separations to take place within each of the chambers 822a, 822b.

The embodiment of FIG. 14 allows for multiple particle separations to take place simultaneously. Additionally, different types of particles may be harvested in one single procedure. Of course, one or more further fluid chambers may be added without departing from the scope of the invention. Furthermore, both of the chambers 822a and 822b may be cylindrical.

It will be apparent to those skilled in the art that various modifications and variations can be made to the structure and methodology of the present invention without departing from the scope or spirit of the invention.

The fluid chambers 122, 222, 322, 422, 1022, or 1022' depicted in the embodiments of FIGS. 6–9, 16 and 17, may be substituted for the fluid chambers 22, 522, 622, 722, 822a or 822b. Further, the invention can be modified by including supplemental fluid chambers or separation chambers. Although the invention has been described as having a separation chamber to initially separate particles from the liquid, the invention can be practiced without this initial separation taking place.

Although the controller 40 is described above as controlling rotor speed and flow rate, the controller 40 may also regulate other parameters. For example the controller may control the density or some other characteristic of the liquid used to carry particles into the fluid chamber.

In addition, while the invention is described herein in connection with blood component separation, the invention in its broadest sense is not so limited. The invention is applicable to other medical and non-medical uses.

The particles used to form the saturated fluidized bed in the fluid chamber can differ from the particles within the fluid passing through the fluid chamber for filtration. Additionally, it is possible to initially form the saturated fluidized bed with an extremely high concentration of platelets having very few white blood cells.

Further, the fluid chamber of the invention may be used in a separation process involving elutriation or any other particle separation means without departing from the scope of the invention.

Figure 18:
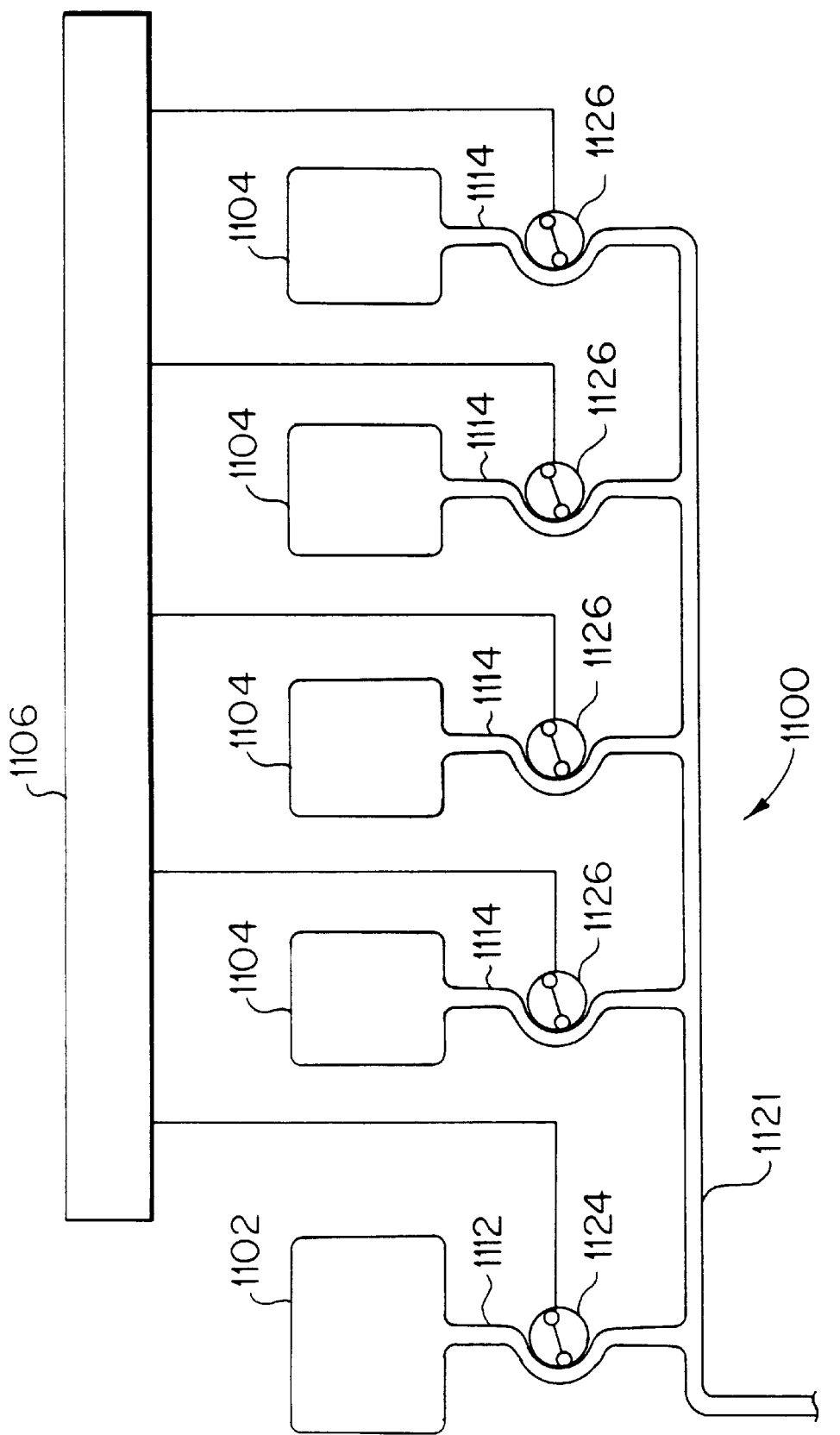
FIG. 18 is a schematic diagram of an embodiment of the invention including a fluid supply line coupled to a primary substance container and additive containers.
Figure 19:
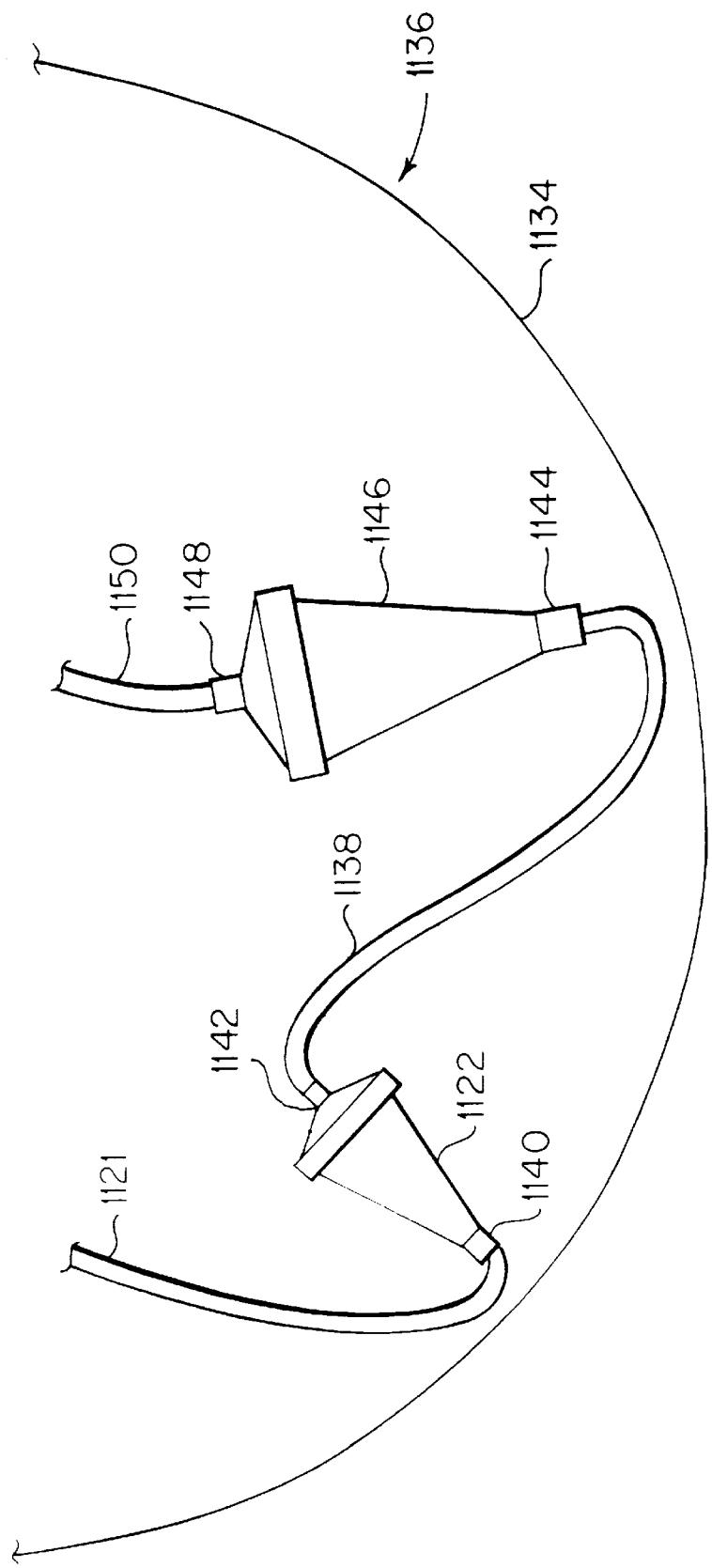
FIG. 19 is a partial schematic diagram of a centrifuge apparatus including a fluid chamber and supplemental fluid chamber in accordance with an embodiment of the invention.
Figure 20:
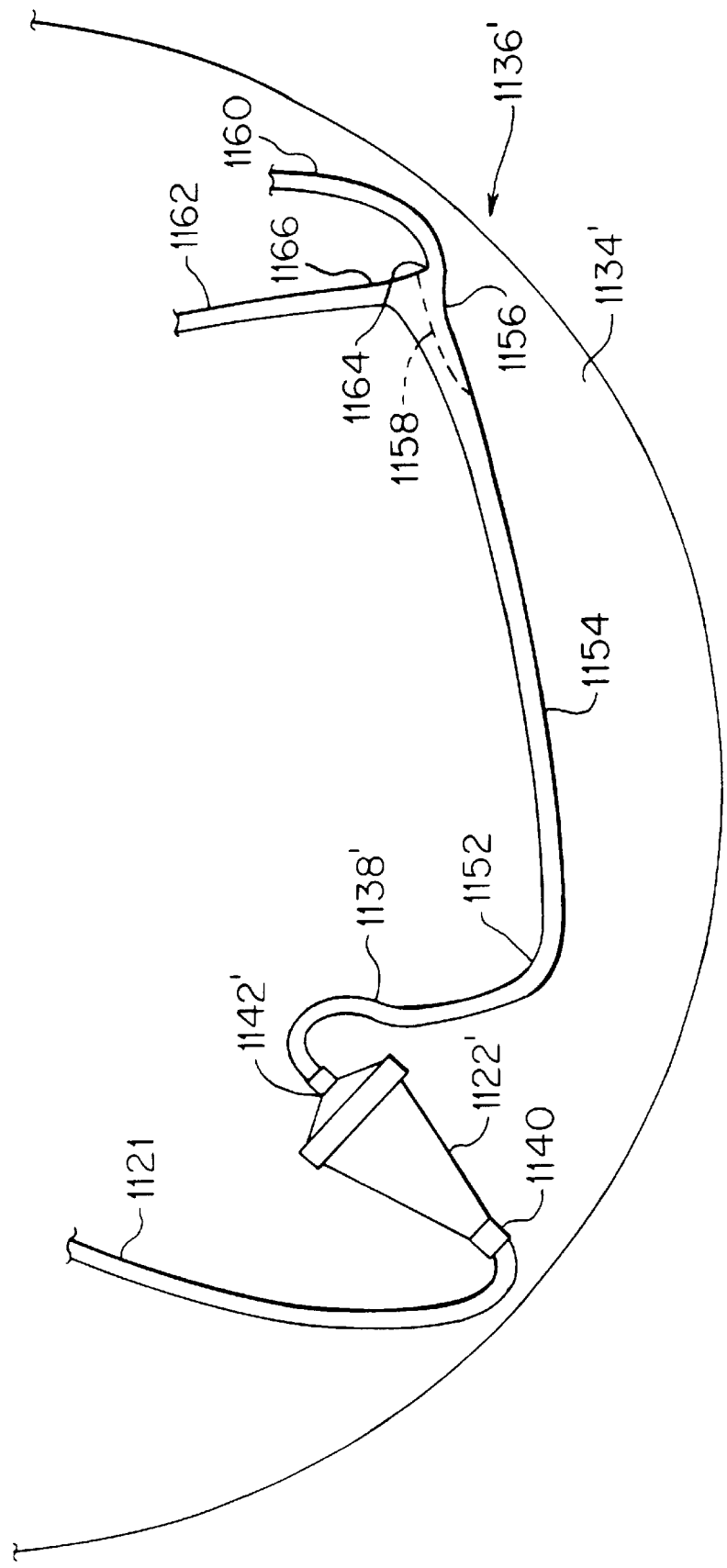
FIG. 20 is a partial schematic diagram of a centrifuge apparatus including a fluid chamber and separation channel in accordance with the invention.

In accordance with the invention there is also provided means for altering sedimentation velocity of particles used to form the saturated bed. FIGS. 18–20 illustrate embodiments of the invention including examples of such means. As illustrated in FIG. 18, a portion of a tubing set 1100 preferably includes a primary container 1102 for containing a primary substance including liquid and particles to be separated.

In a preferred embodiment of the invention, the primary substance in primary container 1102 is a peripheral cell collection including, for example, plasma, red blood cells, stem cells, T cells and optionally tumor cells. As mentioned above, devices for purifying blood to obtain a peripheral cell collection are known in the art. As described in more detail below, particular particles, such as red blood cells, in the primary substance are used to form a saturated fluidized particle bed in a fluid chamber 1122 or 1122' shown respectively in FIGS. 19 and 20. Fluid chambers 1122 and 1122' are preferably constructed in a manner similar to one of the fluid chambers 22, 122, 222, 322, 422, 522, 622, 722, 822a, 822b, 1022, or 1022' described above.

As shown in FIG. 18, the tubing set 1100 also preferably includes a series of additive containers 1104 containing additives for altering sedimentation velocity of the particles in the primary substance forming the saturated fluidized bed in the fluid chamber 1122, 1122'. A series of outflow tubes 1112 and 1114 respectively couple the primary container 1102 and each of the additive containers 1104 to a supply line 1121 of the tubing set 1100 so that the primary substance and additives flowing in the outflow tubes 1112 and 1114 mix in the supply line 1121. As shown respectively in FIGS. 19 and 20, the supply line 1121 is coupled to an inlet 1140, 1140' of the fluid chamber 1222, 1222' (respectively).

A series of pumps 1124 and 1126, shown schematically in FIG. 18, regulate flow in the outflow tubes 1112 and 1114 from the primary container 1102 and additive containers 1104 to the supply line 1121. Preferably, the pumps 1124 and 1126 are peristaltic pumps connected to a controller 1106, similar to the controller 40 described above in connection with FIG. 3. Controller 1106 meters the amount of primary substance and additives flowing and mixing in the supply line 1121.

As will be recognized by those skilled in the art, other types of flow regulating devices, such as, for example, valves or impeller pumps, could be used in place of the peristaltic pumps 1124 and 1126. In its broadest sense, the invention does not require all of the above-described structure. For example, the additive substances could be introduced directly into the primary container 1102 without the use additive containers 1104, pumps 1126, and outflow tubes 1114. When the particles forming the saturated fluidized bed are magnetic, a variable magnetic field adjacent to the fluid chamber 1122, 1122' could alter sedimentation velocity of the bed forming particles.

With the structure described above, it is possible to alter the sedimentation velocity of particles forming a saturated fluidized bed in chamber 1122, 1122'. By changing sedimentation velocity, as described below, filtration characteristics of the saturated fluidized bed may be altered.

In use, one or more of the additive substances in containers 1104 are chosen because of their ability to change the sedimentation velocity of the bed forming particles to a sedimentation velocity greater than that of first particles in the primary substance and less than that of second particles in the primary substance. Controller 1106 regulates pumps 1126 to precisely control the sedimentation velocity of the particles in the saturated fluidized bed. After the sedimentation velocity of the bed forming particles in properly adjusted, the bed allows certain particles to pass through the fluid chamber 1122, 1122' while other particles are retained by the bed in fluid chamber 1122, 1122'.

When sedimentation velocity of the bed forming particles is decreased, the saturated fluidized bed retains particles in the fluid chamber 1122 or 1122' that would normally pass through the bed if the sedimentation velocity of the bed forming particles was not altered. Conversely, when sedimentation velocity of the bed forming particles is increased, the saturated fluidized bed allows particles to pass through the bed that would normally be retained in the fluid chamber 1122 or 1122' if the sedimentation velocity of the bed forming particles was not altered.

In a preferred embodiment of the invention, red blood cells may be used to form the saturated fluidized bed, and one of the additive containers 1104 may contain an additive substance such as water or saline having a weak concentration of salt. For example, the additive substance in one of the additive containers 1104 may be a saline solution having about 0.4% sodium chloride by weight. Such additive substances are hypotonic as compared to red blood cells. Another of the additive containers 1104, preferably contains an additive substance, such as saline having a strong concentration of salt, which is hypertonic as compared to red blood cells. For example, the hypertonic additive solution in one of the additive containers 1104 may be a saline solution having about 7% sodium chloride by weight.

The hypotonic or hypotonic additive substances may be many different types of solutions containing a predetermined concentration of a particular solute. For example, these substances may include albumin as a solute.

As described in more detail below, hypotonic additive solutions tend to osmotically increase the size of red blood cells. Conversely, hypertonic solutions tend to osmotically decrease red blood cell size. Particle sedimentation velocity, as previously discussed, is directly related to the size of the particle according to Stokes law. Therefore, an increase in particle size increases sedimentation velocity, while a decrease in particle size decreases sedimentation velocity.

Another of the additive containers 1104 preferably holds a solution containing albumin or sucrose. Such solutions change the density and/or viscosity of liquid, such as plasma, flowing from the primary container 1102. As mentioned above, sedimentation velocity of a particle is also related to the density and viscosity of a fluid according to Stoke's law. Therefore, by adding density/viscosity altering compounds into supply line 1121, sedimentation velocity of the saturated fluidized bed particles may be altered.

At least one of the additive containers 1104 preferably contains a substance that links a number of the saturated fluidized bed forming particles in the primary solution together to form a series of saturated bed forming particle groups having a size larger than that of the individual particles. Because the particles groups are larger than the individual particles, sedimentation velocity of the saturated bed forming particle groups is greater than that of the individual particles according to Stoke's law. In a preferred embodiment, such a particle group forming substance contains macromolecules of dextran or fibrogen. These substances cause red blood cells to rouleau—that is the red blood cells link together and form separate red blood cell groups.

In an embodiment of the invention shown in FIG. 19, the supply line 1121 is coupled to the inlet 1140 of fluid chamber 1122. The fluid chamber 1122 is mounted to a centrifuge rotor 1134 of a centrifuge device 1136 preferably including a motor, shaft, arm, holder, pump, and controller 1106 respectively similar or identical to the motor 16, shaft 18, arm 19, holder 24, pump 36, and controller 40 shown in FIGS. 1 and 3.

In an alternate embodiment of the invention shown in FIG. 20, the supply line 1121 is coupled to an inlet 1140' of fluid chamber 1122'. The fluid chamber 1122' is mounted to a centrifuge rotor 1134' of a centrifuge device 1136' configured like the centrifuge device 1136 shown in FIG. 19.

In accordance with the invention there is also provided means for separating particles from liquid after the particles and liquid flow from the fluid chamber. As illustrated in FIG. 19, intermediate tubing 1138 couples an outlet 1142 of fluid chamber 1122 to an inlet 1144 of a supplemental chamber 1146. Supplemental chamber 1146 is removably mounted on the centrifuge rotor 1134.

As shown in FIG. 19, the fluid chamber 1122 and supplemental chamber 1146 are spaced at approximately the same distance from an axis of rotation of rotor 1134. A maximum cross-sectional area of the supplemental chamber 1146 is preferably larger than that of the fluid chamber 1122 so that the supplemental chamber 1146 retains particles without forming a saturated fluidized particle bed. In an alternate embodiment (not shown), the supplemental chamber 1146 is further than fluid chamber 1122 from an axis of rotation of rotor 1134. During rotation of rotor 1134, this spacing allows particles in the supplemental chamber 1146 to encounter a stronger centrifugal force than particles in fluid chamber 1122, thus allowing the supplemental chamber 1146 to have a maximum cross sectional area similar to that of fluid chamber 1122.

As described in more detail below, by controlling flow rate and rotation of rotor 1134, centrifugal force in the supplemental chamber 1146 causes particles passing from fluid chamber 1122 to be retained in chamber 1146 while permitting liquid to pass through an outlet 1148 and into an outlet line 1150.

As shown in FIG. 19, the supplemental chamber 1146 is preferably larger than the fluid chamber 1122, permitting the supplemental chamber 1146 to retain a substantial number of particles. Preferably, an interior of the supplemental chamber 1146 is shaped like that of the fluid chamber 1122.

In an alternate embodiment shown in FIG. 20, intermediate tubing 1138' couples an outlet 1142' of fluid chamber 1122' to an inlet 1152 of a separation channel 1154 mounted to centrifuge rotor 1134'. Adjacent to an outer portion of the centrifuge rotor 1134', the separation channel 1154 has a collection well 1156 for collecting particles flowing into the separation channel 1154. Rotation of centrifuge rotor 1134' sediments particles into the collection well 1156 while slower sedimenting liquid and possibly some slower sedimenting particles remain above a top boundary 1158 of the collection well.

As shown in FIG. 20, collection well 1156 has a particle concentrate outlet 1164 connected to a particle concentrate line 1160. The particle concentrate line 1160 removes particles retained in the collection well 1156. A liquid outlet 1166 is provided above top boundary 1158 and is connected to liquid outlet line 1162. The liquid outlet line 1162 removes liquid above the top boundary 1158. In addition, the liquid outlet line 1162 may remove slower sedimenting particles above the top boundary 1158.

Preferably, the particle collection well 1156, particle concentrate outlet 1164 and liquid outlet 1166 are located at or adjacent to one end of the separation channel 1154, and the inlet 1152 is located at or adjacent to an opposite end of the separation channel 1154. This spacing ensures ample time for separation of particles from liquid, collection of a substantial number of particles in the collection well 1156, and corresponding removal of a substantial number of particles through the concentrate line 1160.

Methods for separating T cells, tumor cells, stem cells, and/or plasma from a peripheral cell collection are discussed below with reference to FIGS. 18–20. Although the invention is described in connection with separating these substances from a peripheral cell collection, it should be understood that the invention in its broadest sense is not so limited. For example, the invention may be readily practiced to separate substances in a bone marrow harvest collection or an umbilical cord cell collection harvested following birth. In addition, the method of the invention in its broadest sense could be practiced with structure different from that described in connection the embodiments shown in FIGS. 18–20.

After a donation procedure in which a peripheral cell collection is obtained, the peripheral cell collection is placed in the primary container 1102. A substantial portion of the peripheral cell collection includes plasma, red blood cells, stem cells, and T cells. If the donor's blood included tumor cells, these cells are also present in the peripheral cell collection.

Ultimately, the red blood cells from the peripheral cell collection will be used to form a saturated fluidized bed in the fluid chamber 1122, 1122'. If the number of red blood cells in the peripheral cell collection is insufficient to form the saturated bed, additional red blood cells are preferably added to the primary container 1102 so that the number of red blood cells exceeds the number of stem cells, T cells, and any tumor cells in the primary container 1102.

At the beginning of a particle separation procedure, the pump 1124 associated with container 1102 is activated to convey the peripheral cell collection from the primary container 1102 to the supply line 1121. In addition, one or more of pumps 1126 associated with the additive substances from additive containers 1104 are used to supply additives to supply line 1121. In the supply line 1121, the peripheral cell collection and one or more of the additive substances mix to increase or decrease the sedimentation velocity of the red blood cells.

When hypotonic solution is added to supply line 1121, the red blood cells osmotically increase in size thereby increasing the sedimentation velocity of the red blood cells. Conversely, when the hypotonic solution is added to supply line 1121, the red blood cells decrease in size thereby reducing the sedimentation velocity of the red blood cells. When saline is used as the hypotonic or hypertonic solution, the mixture of the peripheral cell collection and additive substances in supply line 1121 may include about 0.6% to about 5% sodium chloride by weight. Preferably, the amount of sodium chloride or other solutes in the supply line 1121 is sufficient to prevent hemolysis (bursting) of the red blood cells if the red blood cells increase in size. For example, when saline is used, the amount of sodium chloride in the supply line 1121 is preferably above about 0.4% by weight.

When a solution containing albumin or sucrose is added to supply line 1121, the solution increases the density and/or viscosity of plasma in the supply line 1121, thereby reducing sedimentation velocity of the red blood cells. When a medium including macromolecules of dextran or fibrogen are added to the supply line 1121, the medium causes red blood cells in the supply line 1121 to rouleau, thereby increasing the sedimentation velocity of the red blood cells.

The controller 1106 activates one or more of the pumps 1126 depending on the sedimentation velocity of the red blood cells and the sedimentation velocities of cells that will be separated. For example, to separate faster sedimenting stem cells from slower sedimenting T cells, additive introduction is controlled so that the sedimentation velocity of the red blood cells falls between the sedimentation velocity of the stem cells and the sedimentation velocity of the T cells.

The peripheral cell collection and additive substances flow through the supply line 1121 into the inlet 1140, 1140' of the fluid chamber 1122, 1122'. The controller 1106 controls the rotational speed of the rotor 1136, 1136' and the rate of flow into the fluid chamber 1122, 1122' to establish a saturated fluidized bed of red blood cells in the fluid chamber 1122, 1122'.

The saturated fluidized bed of red blood cells behaves like the earlier-described saturated fluidized bed of platelets. Plasma, additive substances, and slower sedimenting T cells pass through the saturated fluidized red blood cell bed and outlet 1142, 1142', while the bed retains faster sedimenting stem cells in the fluid chamber 1122, 1122'. As red blood cells continue to flow into the fluid chamber 1122, 1122' and enter the saturated fluidized bed, red blood cells flow from the outlet 1142, 1142'. Because the fluidized bed is saturated, the rate at which red blood cells enter the inlet 1140, 1140' equals the rate at which red blood cells pass through the outlet 1142, 1142'.

As the saturated fluidized red blood cell bed continues to filter faster sedimenting particles, the pump 1124 and one or more of additive pumps 1126 continue to mix the peripheral cell collection and additives in the supply line 1121. This ensures that red blood cells entering the saturated fluidized bed and red blood cells in the bed have a sedimentation velocity between that of the first and second particles being separated.

In the embodiment of FIG. 19, plasma, additive substances, T cells, and the portion of red blood cells leaving the saturated fluidized bed flow through the outlet 1142 and intermediate tubing 1138 into the inlet 1144 of supplemental chamber 1146. In the supplemental chamber 1146, centrifugal force caused by rotation of the rotor 1134 retains the T cells and red blood cells. Meanwhile, the plasma and additives substances flow from the outlet 1148 into the outlet line 1150. This separates the T cells and red blood cells from the plasma and additive substances.

The stem cells and red blood cells in the fluid chamber 1122 and the T cells and red blood cells in the supplemental chamber 1146 may retain a residue of some of the additive substances, such as albumin, sucrose, dextran, or fibrogen.

To wash this residue from these cells, one of pumps 1126 preferably pumps a washing medium such as saline from a corresponding additive container 1104 through the fluid chamber 1122 and supplemental fluid chamber 1146 before completion of the separation procedure. If necessary, rotational speed of the rotor 1134 may be altered to retain particles in the fluid chamber 1122 and supplemental fluid chamber 1146 during washing.

When all of the peripheral cell collection flows from primary container 1102, the controller 1106 terminates rotation of the centrifuge rotor 1134. To remove the stem cells and red blood cells from the fluid chamber 1222, a procedurist releases the fluid chamber 1122 from the centrifuge rotor 1134 and separates the supply line 1121 or intermediate tubing 1138 from the fluid chamber 1122. In a similar fashion, the procedurist removes T cells and red blood cells retained in the supplemental fluid chamber 1146.

In the embodiment of FIG. 20, plasma, additive substances T cells, and the portion of red blood cells leaving the saturated fluidized bed flow through the outlet 1142' and intermediate tubing 1138' into the inlet 1152 of separation channel 1154. Centrifugal force generated by the rotation of centrifuge rotor 1134' sediments the T cells and red blood cells in the collection well 1156, while plasma and additive substances remain above the top boundary 1158 of the collection well 1156. As the T cells and red blood cells collect in the collection well 1156, the particle concentrate line 1160 removes them through outlet 1164. Simultaneously, the liquid outlet line 1162 removes plasma and additive substances through the liquid outlet 1166.

When the primary container 1102 empties, the controller 1106 terminates rotation of the rotor 1136'. A procedurist then removes the stem cells and red blood cells from the fluid chamber 1222' by releasing the fluid chamber 1122' from the centrifuge rotor 1134' and separating the supply line 1121' or intermediate tubing 1138' from the fluid chamber 1122'.

To separate faster sedimenting tumor cells from slower sedimenting stem cells, one or more of the pumps 1126 add additive substances from one or more of the additive containers 1104 into the supply line 1121. The additive substances adjust the sedimentation velocity of the red blood cells to a sedimentation velocity between the sedimentation velocity of tumor cells and the sedimentation velocity of stem cells.

As described above, a saturated fluidized bed of red blood cells forms in the fluid chamber 1122, 1122'. Because the tumor cells have a sedimentation velocity greater than that of the red blood cells, the saturated fluidized red blood cell bed retains tumor cells in the fluid chamber 1122, 1122'. Stem cells, which now have a sedimentation velocity less than that of the red blood cells, flow from the outlet 1142, 1142' of fluid chamber 1122, 1122' along with the portion of red blood cells leaving the bed.

In the supplemental chamber 1146 or the separation channel 1154, stem cells and red blood cells separate from the plasma and additive substances in the same way the T cells and red blood cells separate from the plasma and additive substances in the method described above. When the embodiment of FIG. 19 is used, washing medium, such as saline from one of additive containers 1104, preferably washes additive residue from the particles in fluid chamber 1122, and in supplemental fluid chamber 1146, as described above.

When the primary container 1102 is empty, a procedurist removes tumor cells and red blood cells from the fluid chamber 1122 or 1122'. Stem cells and the red blood cells are removed from the supplemental chamber 1146 shown in FIG. 19 or from the particle concentrate outlet shown in FIG. 20.

The invention may be used to separate slower sedimenting tumor cells from faster sedimenting stem cells by retaining stem cells in the saturated fluidized red blood cell bed, while allowing tumor cells to pass through the bed. The invention, in is broadest sense, may also be used to separate many different types of particles from one another. Thus, it should be understood that the invention is not limited to the examples discussed in this specification. Rather the invention is intended to cover modifications and variations provided they come within the scope of the following claims and their equivalents.

What is claimed is:

1. A method of separating first particles from second particles, the method comprising the steps of:

rotating a centrifuge rotor about an axis of rotation, the rotor having an associated fluid chamber rotatable therewith, the fluid chamber having an inlet and an outlet;

controlling rotation of the rotor;

altering sedimentation velocity of the first particles;

passing a quantity of the first particles into the inlet of the rotating fluid chamber;

forming, with the first particles, a saturated fluidized bed within the fluid chamber; and flowing into the fluid chamber inlet liquid having at least a quantity of the second particles dispersed therein while simultaneously maintaining the bed within the fluid chamber, so that the bed substantially prevents flow of the second particles from the fluid chamber inlet to the fluid chamber outlet while substantially permitting flow of the liquid and a portion of the first particles to the outlet.

2. The method of claim 1, wherein the liquid in the step of flowing additionally includes first particles disbursed therein.

3. The method of claim 1, wherein the first particles include red blood cells, and the second particles include cells chosen from a group consisting of stem cells and tumor cells.

4. The method of claim 1, further comprising the step of removing second particles retained in the fluid chamber.

5. The method of claim 1 wherein the altering step includes the substep of changing size of the first particles.

6. The method of claim 1, wherein the altering step includes the substep of contacting the first particles with a solution that is hypertonic as compared to the first particles so that osmosis decreases size of the first particles.

7. The method of claim 1, wherein the altering step includes the substep of contacting the first particles with a solution that is hypotonic as compared to the first particles so that osmosis increases size of the first particles.

8. The method of claim 1, wherein the altering step includes the substep of changing tonicity of the liquid so that osmosis decreases size of the first particles.

9. The method of claim 1, wherein the altering step includes the substep of changing tonicity of the liquid so that osmosis increases size of the first particles.

10. The method of claim 1, wherein the altering step includes the substep of changing at least one of density and viscosity of the liquid.

11. The method of claim 1, wherein the altering step includes the substep of linking a number of the first particles to form a series of first particle groups.

12. The method of claim 1, wherein the first particles are red blood cells, and wherein the altering step includes the substep of contacting the red blood cells with a substance for causing the red blood cells to rouleau.

13. The method of claim 1, wherein the altering step precedes the flowing step.

14. The method of claim 1, wherein at least a portion of the altering step is simultaneously conducted with the flowing step.

15. The method of claim 1, further comprising the step of separating the portion of the first particles flowing to the outlet of the fluid chamber from the liquid flowing to the outlet of the fluid chamber.

16. A method of separating first particles from second particles, the method comprising the steps of:

rotating a centrifuge rotor about an axis of rotation, the rotor having an associated fluid chamber rotatable therewith, the fluid chamber having an inlet and an outlet;

controlling rotation of the rotor;

altering sedimentation velocity of the first particles;

passing a quantity of the first particles into the inlet of the rotating fluid chamber;

forming, with the first particles, a saturated fluidized bed within the fluid chamber;

flowing into the fluid chamber inlet liquid having at least a quantity of the second particles dispersed therein while simultaneously maintaining the bed within the fluid chamber, so that the bed substantially prevents flow of the second particles from the fluid chamber inlet to the fluid chamber outlet while substantially permitting flow of the liquid and a portion of the first particles from the outlet; and separating the portion of the first particles flowing from the outlet of the fluid chamber from the liquid flowing from the outlet of the fluid chamber.

17. An apparatus for separating first particles from second particles, the apparatus comprising:

a motor;

a centrifuge rotor coupled to the motor for rotation about an axis of rotation;

a holder for holding a fluid chamber on the rotor with an outlet of the fluid chamber positioned closer to the axis of rotation than an inlet of the fluid chamber;

means for supplying liquid and first and second particles to the inlet of the fluid chamber;

means for altering sedimentation velocity of the first particles; and means for controlling at least one of the motor and the supplying means to maintain a saturated fluidized bed of first particles within the fluid chamber and to cause second particles to be retained in the fluid chamber.

18. The apparatus of claim 17, wherein the means for altering sedimentation velocity of the first particles includes means for adjusting tonicity of the liquid to osmotically change size of the first particles.

19. The apparatus of claim 17, wherein the means for altering sedimentation velocity of the first particles includes means for adjusting at least one of density and viscosity of the liquid.

20. The apparatus of claim 17, wherein the means for altering sedimentation velocity of the first particles includes means for linking together first particles to form a series of first particle groups.

21. The apparatus of claim 17, further comprising a fluid chamber in the holder and means for separating particles flowing from the outlet in the fluid chamber from liquid flowing from the outlet of the fluid chamber.

22. The apparatus of claim 21, wherein the means for separating particles includes a supplemental chamber having an inlet in fluid communication with the outlet of the fluid chamber.

23. The apparatus of claim 21, wherein the means for separating particles includes a separation channel having a collection well for retaining particles therein, the separation channel including an inlet, a particle concentrate outlet located in the collection well, and a liquid outlet located in a portion of the separation channel outside of the collection well, the inlet of the separation channel being flow connected to the outlet of the fluid chamber.

24. An apparatus for separating first particles from second particles, the apparatus comprising:

a motor;

a centrifuge rotor coupled to the motor for rotation about an axis of rotation;

a fluid chamber connected to the rotor, the fluid chamber having an inlet and an outlet;

means for supplying liquid and first and second particles to the inlet of the fluid chamber;

means for controlling at least one of the motor and the supplying means to maintain a saturated fluidized bed of first particles within the fluid chamber and to cause second particles to be retained in the fluid chamber; and means for separating particles flowing from the outlet of the fluid chamber from liquid flowing from the outlet of the fluid chamber.

25. The apparatus of claim 24, wherein the means for separating particles includes a supplemental chamber having an inlet in fluid communication with the outlet of the fluid chamber.

26. The apparatus of claim 24, wherein the means for separating particles includes a separation channel having a collection well for retaining particles therein, the separation channel including an inlet, a particle concentrate outlet located in the collection well, and a liquid outlet located in a portion of the separation channel outside of the collection well, the inlet of the separation channel being flow connected to the outlet of the fluid chamber.

27. The apparatus of claim 17, comprising means for separating particles flowing from the outlet of the fluid chamber from liquid flowing from the outlet of the fluid chamber.

28. The apparatus of claim 24, further comprising a holder for holding the fluid chamber on the rotor.

29. The apparatus of claim 24, further comprising means for altering sedimentation velocity of the first particles.

* * * * *